(12) United States Patent
Grot et al.

(10) Patent No.: US 9,915,612 B2
(45) Date of Patent: Mar. 13, 2018

(54) ARRAYS OF INTEGRATED ANALYTICAL DEVICES

(71) Applicant: Pacific Biosciences of California, Inc., Menlo Park, CA (US)

(72) Inventors: Annette Grot, Cupertino, CA (US); Ravi Saxena, Millbrae, CA (US); Paul Lundquist, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/451,305

(22) Filed: Mar. 6, 2017

(65) Prior Publication Data

US 2017/0176335 A1 Jun. 22, 2017

Related U.S. Application Data

(63) Continuation of application No. 14/836,629, filed on Aug. 26, 2015, now Pat. No. 9,606,068.
(Continued)

(51) Int. Cl.
*G01N 21/64* (2006.01)
*H01L 27/146* (2006.01)
(Continued)

(52) U.S. Cl.
CPC ....... *G01N 21/6454* (2013.01); *G01N 21/648* (2013.01); *G01N 21/6428* (2013.01);
(Continued)

(58) Field of Classification Search
CPC .......... G01N 21/78; G01N 2021/7756; G01N 21/6454; G01N 21/648; G01N 21/6428;
(Continued)

(56) References Cited

U.S. PATENT DOCUMENTS

| 4,645,523 A | 2/1987 | Howard et al. |
| 5,082,629 A | 1/1992 | Burgess, Jr. et al. |

(Continued)

FOREIGN PATENT DOCUMENTS

| EP | 1105529 B1 | 11/2005 |
| EP | 1871902 B1 | 10/2006 |

(Continued)

OTHER PUBLICATIONS

Abbas et al. (2011) Sens. Actuators B Chem. 156:169-175.
(Continued)

*Primary Examiner* — Sang Nguyen
(74) *Attorney, Agent, or Firm* — VLP Law Group LLP

(57) ABSTRACT

Arrays of integrated analytical devices and their methods for production are provided. The arrays are useful in the analysis of highly multiplexed optical reactions in large numbers at high densities, including biochemical reactions, such as nucleic acid sequencing reactions. The devices allow the highly sensitive discrimination of optical signals using features such as spectra, amplitude, and time resolution, or combinations thereof. The devices include an integrated diffractive beam shaping element that provides for the spatial separation of light emitted from the optical reactions.

32 Claims, 42 Drawing Sheets

Related U.S. Application Data

(60) Provisional application No. 62/042,793, filed on Aug. 27, 2014.

(51) Int. Cl.

| | | |
|---|---|---|
| *G02B 6/136* | (2006.01) | |
| *G01N 21/77* | (2006.01) | |
| *G02B 6/132* | (2006.01) | |
| *G02B 6/12* | (2006.01) | |

(52) U.S. Cl.
CPC ......... *G01N 21/7703* (2013.01); *G02B 6/132* (2013.01); *G02B 6/136* (2013.01); *H01L 27/14621* (2013.01); *H01L 27/14627* (2013.01); *H01L 27/14685* (2013.01); *G01N 2021/6439* (2013.01); *G01N 2021/6478* (2013.01); *G01N 2021/7786* (2013.01); *G01N 2201/0873* (2013.01); *G02B 2006/12102* (2013.01); *G02B 2006/12109* (2013.01)

(58) Field of Classification Search
CPC .. G02B 5/1895; G02B 5/201; G02B 27/4244; G02B 27/4238; H01L 27/4685
See application file for complete search history.

(56) References Cited

U.S. PATENT DOCUMENTS

| | | |
|---|---|---|
| 5,094,517 A | 3/1992 | Franke |
| 5,135,876 A | 8/1992 | Andrade et al. |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead et al. |
| 5,919,712 A | 7/1999 | Herron et al. |
| 6,002,520 A | 12/1999 | Hoch et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,325,977 B1 | 12/2001 | Theil |
| 6,388,788 B1 | 5/2002 | Harris et al. |
| 6,437,345 B1 | 8/2002 | Bruno-Raumandi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov et al. |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 6,987,613 B2 | 1/2006 | Pocius et al. |
| 7,013,054 B2 | 3/2006 | Levene et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,257,141 B2 | 8/2007 | Chua |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,486,865 B2 | 2/2009 | Foquet et al. |
| 7,499,094 B2 | 3/2009 | Kuriyama |
| 7,537,734 B2 | 5/2009 | Reichert et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,817,281 B2 | 10/2010 | Kiesel et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 7,924,374 B2 | 4/2011 | Chang |
| 8,053,742 B2 | 11/2011 | Lundquist et al. |
| 8,207,509 B2 | 6/2012 | Lundquist et al. |
| 8,247,216 B2 | 8/2012 | Zaccarin et al. |
| 8,274,040 B2 | 9/2012 | Zhong et al. |
| 8,411,375 B2 | 4/2013 | Lenchenkov |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,564,095 B2 | 10/2013 | Huang et al. |
| 8,618,507 B1 | 12/2013 | Lundquist et al. |
| 8,747,751 B2 * | 6/2014 | Duer ............... B01L 3/502715 385/12 |
| 8,906,320 B1 | 12/2014 | Eltoukhy et al. |
| 8,994,946 B2 * | 3/2015 | McCaffrey ........... C12Q 1/6869 356/318 |
| 9,029,802 B2 | 5/2015 | Lundquist et al. |
| 9,223,084 B2 | 12/2015 | Grot et al. |
| 9,372,308 B1 * | 6/2016 | Saxena .............. B29D 17/007 |
| 2002/0034457 A1 | 3/2002 | Reichert et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2003/0044160 A1 | 3/2003 | Jones et al. |
| 2003/0044781 A1 | 3/2003 | Korlach et al. |
| 2003/0132406 A1 | 7/2003 | Waldhausl et al. |
| 2003/0138180 A1 | 7/2003 | Kondo |
| 2003/0174324 A1 | 9/2003 | Sandstrom |
| 2003/0174992 A1 | 9/2003 | Levene et al. |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0006607 A1 | 1/2005 | Winter et al. |
| 2005/0014178 A1 | 1/2005 | Holm-Kennedy |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0103850 A1 | 5/2006 | Alphonse et al. |
| 2007/0036511 A1 | 2/2007 | Lundquist et al. |

(56) References Cited

U.S. PATENT DOCUMENTS

| | | |
|---|---|---|
| 2007/0099212 A1 | 5/2007 | Harris |
| 2007/0134128 A1 | 6/2007 | Korlach |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2008/0002929 A1 | 1/2008 | Bowers et al. |
| 2008/0020938 A1 | 1/2008 | Kaplan |
| 2008/0039339 A1 | 2/2008 | Hassibi et al. |
| 2008/0056950 A1 | 3/2008 | Weisbuch et al. |
| 2008/0161195 A1 | 7/2008 | Turner et al. |
| 2008/0176769 A1 | 7/2008 | Rank et al. |
| 2008/0212960 A1 | 9/2008 | Lundquist et al. |
| 2009/0146076 A1 | 6/2009 | Chiou et al. |
| 2009/0181396 A1 | 7/2009 | Luong et al. |
| 2009/0208957 A1 | 8/2009 | Korlach et al. |
| 2009/0247414 A1 | 10/2009 | Obradovic |
| 2009/0311774 A1 | 12/2009 | Chiou et al. |
| 2010/0065726 A1* | 3/2010 | Zhong .................. G01N 21/648 250/227.24 |
| 2010/0099100 A1 | 4/2010 | Zaccarin et al. |
| 2010/0121582 A1 | 5/2010 | Pan et al. |
| 2010/0163521 A1 | 7/2010 | Balamane et al. |
| 2010/0255488 A1 | 10/2010 | Kong et al. |
| 2010/0256918 A1 | 10/2010 | Chen et al. |
| 2010/0295083 A1 | 11/2010 | Celler |
| 2011/0069389 A1 | 3/2011 | Shpunt |
| 2011/0117637 A1 | 5/2011 | Gray et al. |
| 2011/0183409 A1 | 7/2011 | Newby et al. |
| 2011/0210094 A1 | 9/2011 | Gray et al. |
| 2011/0222179 A1 | 9/2011 | Monadgemi |
| 2011/0223590 A1 | 9/2011 | Chiou et al. |
| 2011/0257040 A1 | 10/2011 | Turner et al. |
| 2011/0306039 A1 | 12/2011 | Chiou et al. |
| 2011/0306143 A1* | 12/2011 | Chiou .................. B82Y 15/00 436/94 |
| 2012/0014837 A1 | 1/2012 | Fehr et al. |
| 2012/0019828 A1 | 1/2012 | McCaffrey et al. |
| 2012/0021525 A1* | 1/2012 | Fehr .................. B01L 3/502707 436/94 |
| 2012/0052506 A1 | 3/2012 | Yue et al. |
| 2012/0058469 A1 | 3/2012 | Shen et al. |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1 | 4/2012 | Zhong et al. |
| 2012/0156100 A1 | 6/2012 | Tsai et al. |
| 2013/0043552 A1 | 2/2013 | Lazarov et al. |
| 2013/0148682 A1 | 6/2013 | Zhang et al. |
| 2013/0338010 A1* | 12/2013 | Turner .................. C12Q 1/6874 506/2 |
| 2014/0193331 A1 | 7/2014 | Naczynski et al. |
| 2014/0241682 A1 | 8/2014 | Sandhu et al. |
| 2014/0287964 A1* | 9/2014 | Lundquist .......... C12Q 1/6874 506/38 |
| 2014/0353577 A1 | 12/2014 | Agarwal et al. |
| 2015/0286060 A1 | 10/2015 | Roh et al. |
| 2016/0154165 A1 | 6/2016 | Grot et al. |
| 2016/0273034 A1 | 9/2016 | Lundquist et al. |

FOREIGN PATENT DOCUMENTS

| | | |
|---|---|---|
| EP | 2362209 A2 | 8/2011 |
| KR | 10-2005-0088782 A | 9/2005 |
| WO | WO 1991006678 A1 | 5/1991 |
| WO | WO 2001016375 A2 | 3/2001 |
| WO | WO 2004100068 A2 | 11/2004 |
| WO | WO 2006116726 A2 | 2/2006 |
| WO | WO 2006135782 A2 | 12/2006 |
| WO | WO 2007002367 A2 | 1/2007 |
| WO | WO 2007011549 A1 | 1/2007 |
| WO | WO 2008002765 A2 | 1/2008 |
| WO | WO 2009056065 A1 | 5/2009 |
| WO | WO 2009131535 A1 | 10/2009 |
| WO | WO 2009149125 A2 | 12/2009 |
| WO | WO 2010051773 A1 | 5/2010 |
| WO | WO 2010102567 A1 | 9/2010 |
| WO | WO 2011076132 A2 | 6/2011 |
| WO | WO 2014031157 A1 | 2/2014 |

OTHER PUBLICATIONS

Barrios (2006) IEEE Photon Technol. Lett. 18:2419.
Barrios et al. (2007) Optics Letters 32:3080.
Barrios et al. (2008) Optics Letters 33:708.
Bernini et al. (2005) Proc. SPIE 5728:101-111.
Boiarski et al. (1992) Proc. SPIE 1793:199-211.
Budach et al. (1999) Anal. Chem. 71(16):3347-3355.
Chen et al. (2012) Optics Letters 37:2814.
Cottier et al. (2002) Proc. SPIE 4616:53-63.
Deopura, M. et al. (2001) Optics Lett 26(15):1197-1199.
Duveneck et al. (2002) Anal Chem Acta 469:49-61.
Eid et al. (2009) Science 323:133.
Feldstein et al. (1999) J. Biomed Microdev. 1:139-153.
Feng et al. (2006) IEEE J. Quantum Electron. 42:885.
Feng et al. (2007) Optics Letters 32:2131.
Fink, Y. et al. (1998) Science 282:1679-1682.
Fonollosa et al. (2006) Proceedings of SPIE 61860R-1: 61860R-11.
Golub (2004) Optics & Photonics News "Laser Beam Splitting by Diffractive Optics" 36-41.
Herron et al. (2003) Biopolymers at Interfaces 2nd Ed, Surfactant Science Series vol. 110, Marcel Dekker, NY pp. 115-163.
Laurell et al. (2012) Optics Express 20:22308.
Leger et al. (1988) The Lincoln Laboratory Journal 1(2):225-246.
Levene, M.J. et al. (2003) Science 299:682-686.
Mortazavi et al. (1994) Optics Letters 19:1290.
Nava et al. (2010) Electronics Letters 46:1686.
Pan et al. (2011) Optics Communications 284:429.
Pang et al. (2011) Lab Chip 11:3698-3702.
Psaltis et al. (2006) Nature 442:381.
Robinson et al. (2008) Optics Express 16:4296.
Sahin et al. (2011) J. Nanophoton. 5:051812.
Salama et al. (2004) Biosensors & Bioelectronics 19:1377-1386.
Song et al. (2012) Optics Express 20:22290.
Sun et al. (2007) Optics Express 15:17967.
Weissman et al. (1999) Proc. SPIE 3596:210-216.
Wu et al. (2006) Biosensors and Bioelectronics 21:1252-1263.
Yao et al. (2012) Nonlinear Optics and Solid-State Lasers, Springer-Verlag Berlin Heidelberg, Chapter 5.
Yariv, a. et al. (1977) IEEE J Quantum Elec QE-13(4):233-253.
International Search Report and Written Opinion dated Dec. 7, 2015 for related PCT/US2015/046985.

* cited by examiner

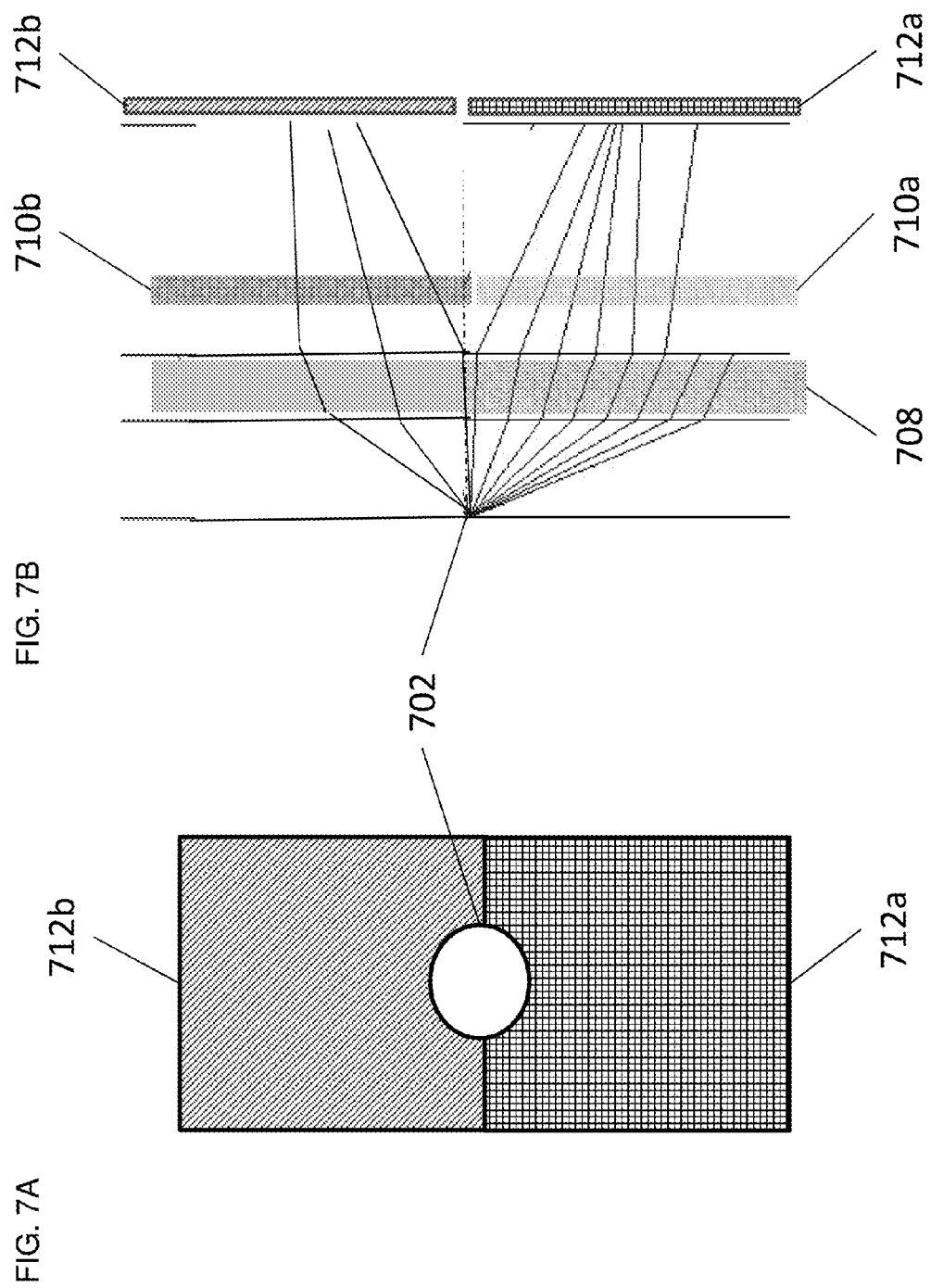

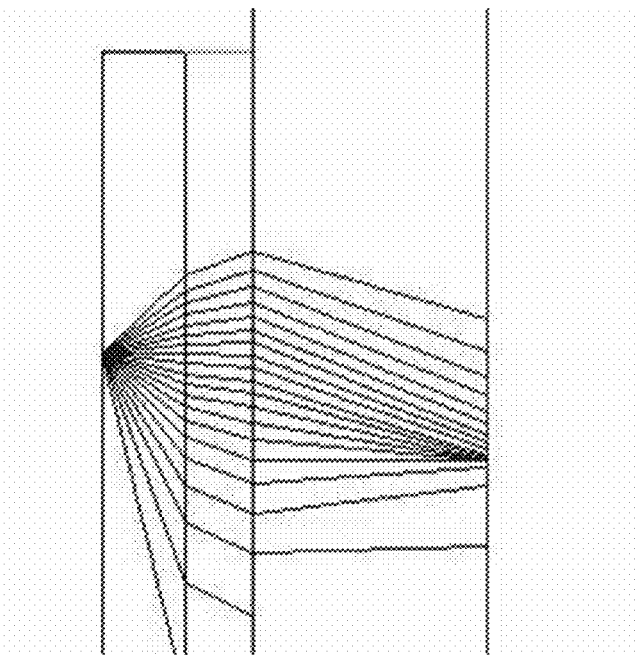
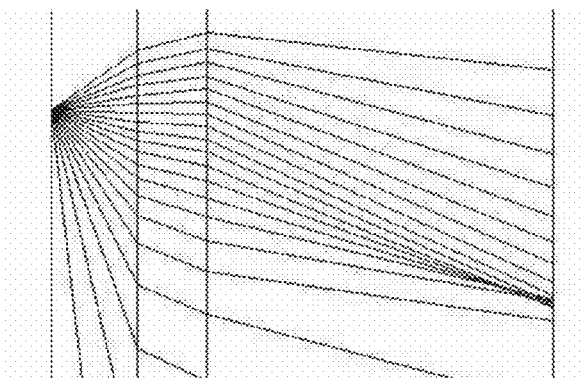
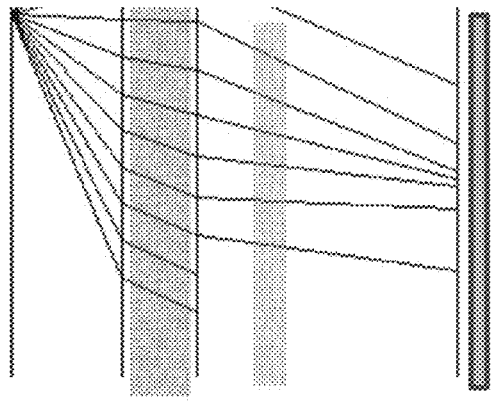
FIG. 8C
FIG. 8B
FIG. 8A

— GaP/TiO$_2$ ~1.128 λ or ~+68, or ~600 nm
— For comparison, TiO$_2$/SiO$_2$ ~ 1.147 λ
• 13 layer pair GaP/TiO$_2$ (H/2 L H/2) design of 42.8 dB of rejection & pass band >622 nm

FIG. 16B

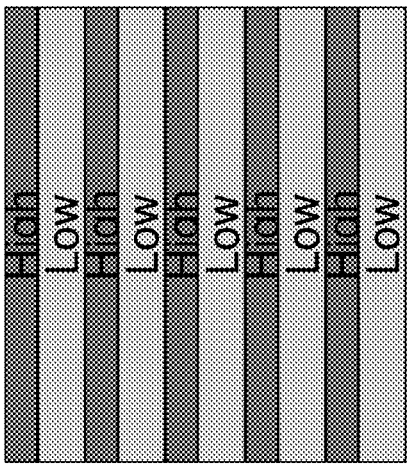

- $y_N = y_s \left(\frac{y_L}{y_H}\right)^{2N}$
- $\rho = \frac{y_m - y_N}{y_m + y_N}$
- $R = \|\rho^2\| \cong 1 - 4\frac{y_N}{y_m}$ (to 1st order in $y_N$)
- $T \equiv 1 - R \cong 4\left(\frac{y_L}{y_H}\right)^{2N}$
- $\log_{10} T \cong \log_{10} 4 + 2N(\log_{10} y_L - \log_{10} y_H)$
  - GaP/TiO$_2$, 13 layer pairs (per approx.) -39.8dB
  - TiO$_2$/SiO$_2$, 11 layer pairs (per approx.) -38.6 dB
  - TiO$_2$/Al$_2$O$_3$, 11 layer pairs (per approx.) -39.7 dB

- $t_{QW} = N \times \frac{\lambda_0}{4}\left(\frac{1}{n_H} + \frac{1}{n_L}\right)$
  - GaP/TiO$_2$, 1236 nm for 13 layer pairs
  - TiO$_2$/SiO$_2$, 1629 nm for 11 layer pairs
  - TiO$_2$/Al$_2$O$_3$, 2054 nm for 15 layer pairs

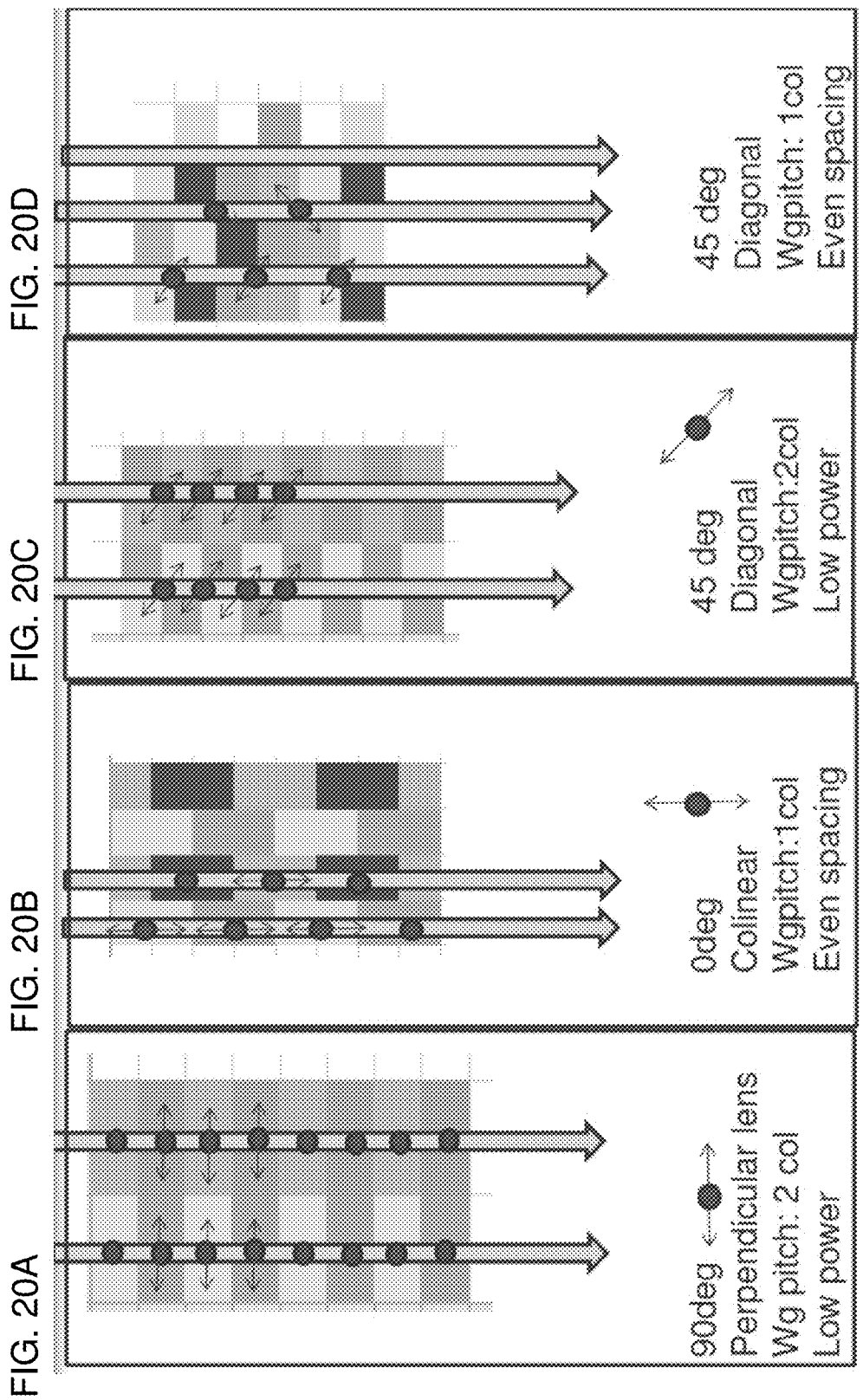

Sensor Substrate

| N | Module Name | Process Description | Specification | Target | ±3σ | Units | Tool Type |
|---|---|---|---|---|---|---|---|
| 1 | CMOS PREP | wet strip | | | | | CINTILLIO |
| 2 | CMOS PREP | HDP oxide dep | Dep Thk | 1.25 | 10% | um | APPLIED, CENTURA |
| 3 | CMOS PREP | oxide cmp | Remaining oxide on metal | 500 | 15% | nm | MIRRA MESA |

Pattern Zero Marks, Aperture 1

| | Module Name | Process Description | Specification | Target | ±3σ | Units | Tool Type |
|---|---|---|---|---|---|---|---|
| 4 | ZERO1 | ZERO1 Litho | minCD ~1.14um | 1.14 | 10% | um | i-Line Litho |
| 5 | ZERO1 | oxide etch | 100nm oxide etch | 100 | 10% | nm | LAM Versys |
| 6 | ZERO1 | wet strip | | | | | SAT2 |
| 7 | APERT1 | Ti/TiN deposition | Dep Thk | 5/100 | 10% | nm | AMAT ENDURA |
| 8 | APERT1 | TiNAP1 Litho | Opening CD | 1 | 10% | um | i-Line Litho |
| 9 | APERT1 | TiN etch + in situ strip | No remaining TiN | 0.1 | 0E | um | LAM TCP 9400 |
| 10 | APERT1 | wet strip | | | | | CINTILLIO |
| 11 | APERT1 | PECVD oxide | Dep Thk | 0.3 | 10% | um | APPLIED, CENTURA |
| 12 | APERT1 | Oxide CMP | Oxide above TiN | 0.1 | 15% | um | MIRRA MESA |

FIG. 26A

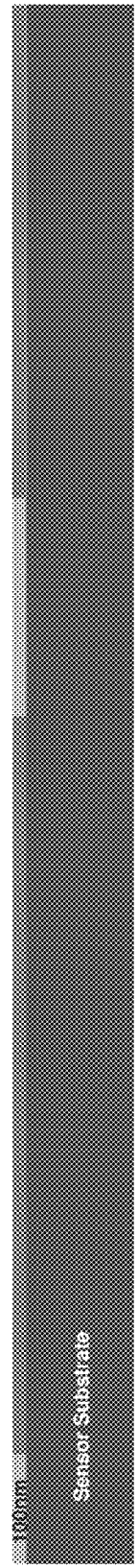

FIG. 26B

Deposit Laser Rejection Filter

| Module Name | Process Description | Specification | | Target | ±3σ | Units | Tool Type |
|---|---|---|---|---|---|---|---|
| 13 | FILTERCF1 | RF deposition - 10 pairs | Dep Thk | 30-130 | 6% | nm | APPLIED, CENTURA |
| 14 | FILTERCF1 | RF+rf1 deposition - 5 pairs | Dep Thk | 30-260 | 6% | nm | APPLIED, CENTURA |
| 15 | FILTERCF1 | Cu back side clean | | | | | SEZ |

Deposit Color Filtration Layer

| | Module Name | Process Description | Specification | Target | ±3σ | Units | Tool Type |
|---|---|---|---|---|---|---|---|
| 16 | FILTERCF1 | CF 1 Litho | Etch Space CD | 2 | 10% | um | i-Line Litho |
| 17 | FILTERCF1 | oxide etch | Post Etch Top Ox Thk | 220 | <10% | nm | LAM Versys |
| 18 | FILTERCF1 | Dry strip | | | | | MATTSON ASPEN |
| 19 | FILTERCF1 | wet strip | | | | | CINTILLIO |
| 20 | FILTERCF2 | CF2 deposition - 3 pairs | Dep Thk | 50-260 | 6% | nm | APPLIED, CENTURA |
| 21 | FILTERCF2 | Cu back side clean | | | | | CINTILLIO |
| 22 | FILTERCF2 | CF 2 Litho | Etch Space CD | 2 | 10% | um | i-Line Litho |
| 23 | FILTERCF2 | oxide etch | Post Etch Top Ox Thk | 220 | <10% | nm | LAM Versys |
| 24 | FILTERCF2 | Dry strip | | | | | MATTSON ASPEN |
| 25 | FILTERCF2 | wet strip | | | | | CINTILLIO |
| 26 | FILTERCF2 | CF2 deposition - last pair | Dep Thk | 50-100 | 6% | nm | APPLIED, CENTURA |

FIG. 26E

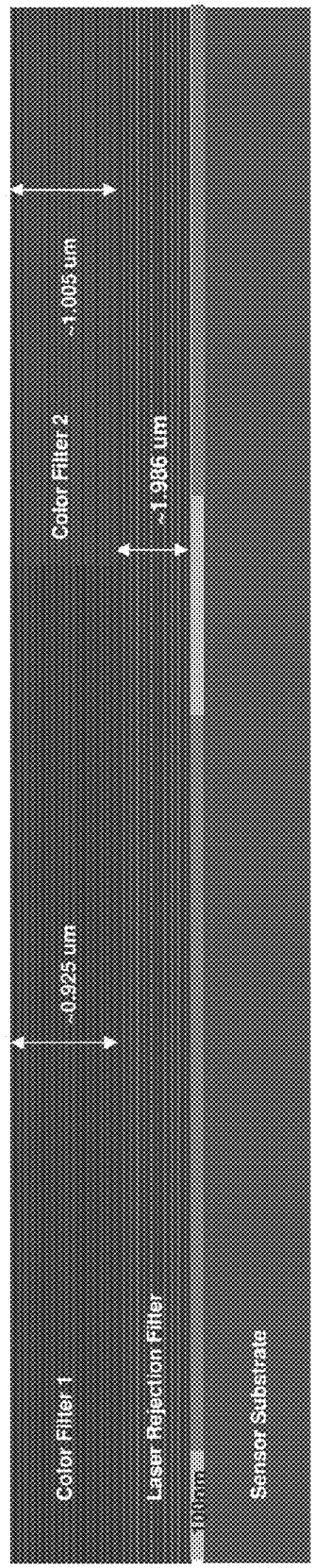

FIG. 26F

| | Module Name | Process Description | Specification | Target | Etho | Units | Tool Type |
|---|---|---|---|---|---|---|---|
| 27 | APERT2 | TiN deposition | Dep Thk | 100 | 10% | nm | AMAT ENDURA |
| 28 | APERT2 | Clearcut Litho | Opens TiN over Zero AM | | | | i-Line Litho |
| 29 | APERT2 | TiN/Al etch | No remaining metal | 100 | OE | | LAM ALLIANCE |
| 30 | APERT2 | TiNAP3 Litho | Opening CD | 1 | 10% | um | i-Line Litho |
| 31 | APERT2 | TiN etch + in situ strip | No remaining TiN | 100 | OE | nm | LAM ALLIANCE |
| 32 | APERT2 | wet strip | | | | | CNTRL10 |
| 33 | LENS | Tensile PECVD oxide dep | Dep Thk | 1.5 | 10% | um | APPLIED, CENTURA |
| 34 | LENS | Compressive PECVD oxide dep | Dep Thk | 1.7 | 10% | um | APPLIED, CENTURA |
| 35 | LENS | Oxide CMP | Remove Thk | 0.1 | 10% | um | MIRRA MESA |
| 36 | LENS | HDP oxide dep | Dep Thk | 0.4 | 10% | um | APPLIED, CENTURA |

FIG. 26G

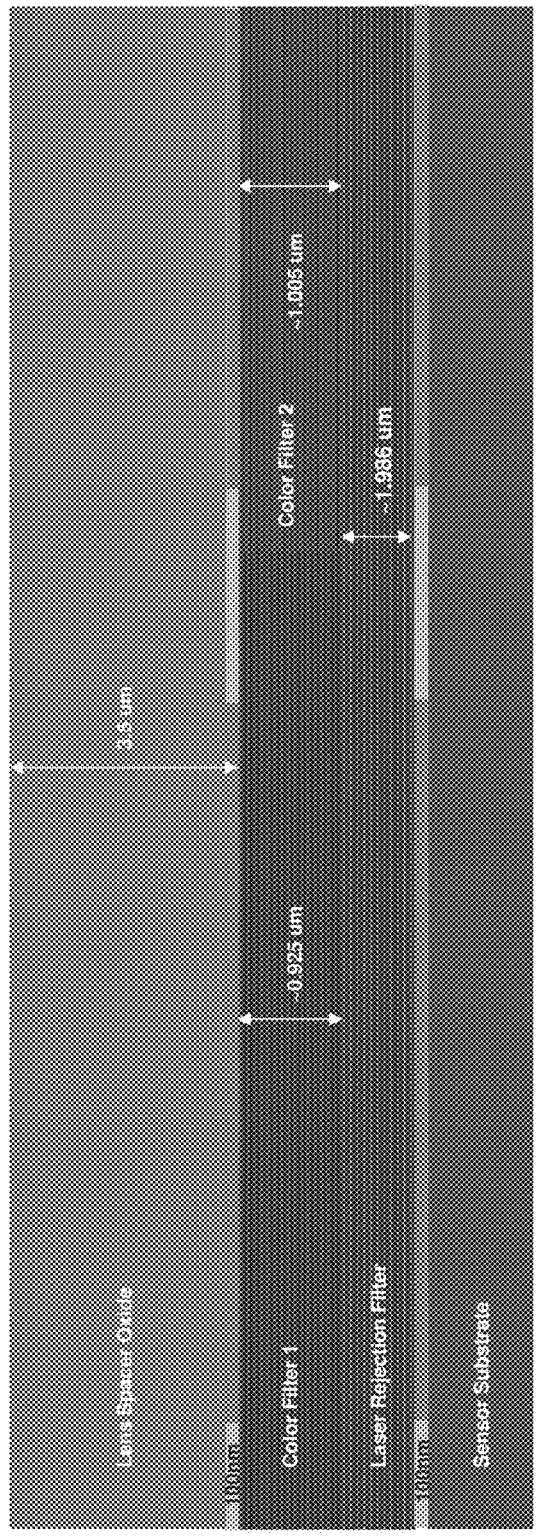

FIG. 26H

| | | | | | |
|---|---|---|---|---|---|
| 37 | LENS | Lens 1 Litho | Resist Space CD | 220 | 10% | nm | 193nm Litho |
| 38 | LENS | BARC etch | | | | | LAM Versys |
| 39 | LENS | oxide etch | Trench Depth | 120 | 10% | nm | LAM ALLIANCE |
| 40 | LENS | Dry strip | | | | | MATTSON ASPEN |
| 41 | LENS | wet strip | | | | | CINTILLIO |
| 42 | LENS | Lens 2 Litho | Resist Space CD | 220 | 10% | nm | 193nm Litho |
| 43 | LENS | BARC etch | | | | | LAM Versys |
| 44 | LENS | oxide etch | Trench Depth | 120 | 10% | nm | LAM ALLIANCE |
| 45 | LENS | Dry strip | | | | | MATTSON ASPEN |
| 46 | LENS | wet strip | | | | | CINTILLIO |
| 47 | LENS | C rich a Si dep | Dep Thk | 0.85 | 10% | um | APPLIED, CENTURA |
| 48 | LENS | SiC CMP | Post Polish Thk | 0.55 | 10% | um | MIRRA MESA |

FIG. 26I

| 49 | APERT3 | ZERO LENS Litho | minCD ~1.14um | 1.14 | 10% | um | I-Line Litho |
| --- | --- | --- | --- | --- | --- | --- | --- |
| 50 | APERT3 | AM a-Si etch_in situstrip | Trench Depth | 100 | 10% | nm | LAM Versys |
| 51 | APERT3 | wet strip | | | | | CINTILLIO |
| 52 | APERT3 | SiN ARC deposition | Dep Thk | 80 | 10% | nm | APPLIED, CENTURA |
| 53 | APERT3 | TiN deposition | Dep Thk | 100 | 10% | nm | AMAT ENDURA |
| 54 | APERT3 | TINAP3 Litho | Opening CD | 1 | 10% | um | I-Line Litho |
| 55 | APERT3 | TiN etch + in situ strip | No remaining TiN | 100 | OE | nm | LAM ALLIANCE |
| 56 | APERT3 | wet strip | | | | | CINTILLIO |

FIG. 26K

| | | | | | | | |
|---|---|---|---|---|---|---|---|
| 57 | REFLECTOR | oxide deposition | Dep Thk | 1.74 | 10% | um | APPLIED, CENTURA |
| 58 | REFLECTOR | Bow measurements | | | | | |
| 59 | REFLECTOR | Ti/TiN/Al | Dep Thk | 5/10/100 | 10% | nm | AMAT ENDURA |
| 60 | REFLECTOR | Clearout Litho | Opens TiN over LenHM AM + ZM5 | | | | I-Line Litho |
| 61 | REFLECTOR | Ti/TiN/Al etch | No remaining metal | 100 | OE | nm | LAM ALLIANCE |
| 62 | REFLECTOR | wet strip | | | | | CINTILLIO |
| 63 | REFLECTOR | Reflector litho | Opening CD | 2 | 10% | um | I-Line Litho |
| 64 | REFLECTOR | Ti/TiN/Al etch | No remaining metal | 100 | OE | nm | LAM ALLIANCE |
| 65 | REFLECTOR | wet strip | | | | | CINTILLIO |
| 66 | REFLECTOR | thickness measurements | oxide on TiNAP3 | TiN/1.69oxide | | | |
| 66 | REFLECTOR | HDP oxide deposition | Dep Thk | 400 | 10% | nm | APPLIED, CENTURA |
| 67 | REFLECTOR | thickness measurements | oxide on reflector | 400 | | nm | |
| 67 | REFLECTOR | oxide CMP | Post Polish Thk | 60 | 10% | nm | MIRRA MESA |
| 68 | REFLECTOR | thickness measurements | oxide on reflector | 60 | | nm | |
| 68 | REFLECTOR | HDP oxide deposition | Dep Thk | 200 | 10% | nm | APPLIED, CENTURA |
| | REFLECTOR | thickness measurements | oxide on reflector | 260 | | nm | |
| | REFLECTOR | Bow measurements | | | | | |
| | REFLECTOR | Defect inspection | | | | | |

FIG. 26M

| | | | | | |
|---|---|---|---|---|---|
| 69 | WG | WG nitride deposition | | | APPLIED, CENTURA |
| | WG | Cu back side clean | | | |
| | WG | thickness measurements | SiN/oxide on reflector | 180*260 | nm |
| 70 | WG | FC Litho | Resist Space CD | 150 | 10% 193nm Litho |
| 71 | WG | SiN etch & in-situ strip | SiN Etch Depth | 115 | 20 nm LAM Versys |
| 72 | WG | Wet strip | | | CINTILLIO |
| | WG | CD measurement | SiN Trench CD | 180 | 36 nm |
| 73 | WG | WG Litho | Resist Line CD | 200 | 10% 193nm Litho |
| 74 | WG | SiN etch & in-situ strip | No remaining SiN | 180 | OE nm LAM Versys |
| 75 | WG | Wet strip | | | CINTILLIO |
| | WG | CD measurement | SiN Line CD | 200 | 10% nm |
| 76 | WG | oxide dep | Dep Thk | 400 | 10% APPLIED, CENTURA |
| | WG | | oxide on reflector | 640nm oxide | nm |
| 77 | WG | CIS oxide cmp | Post Polish Thk above SiN | 50 | 10% MIRRA MESA |
| | WG | | oxide on reflector | 490nm oxide | nm |
| | WG | thickness measurements | | | |
| | WG | Defect inspection | | | |
| 78 | WG | oxide dep | Post Dep Thk above SiN | 250 | 10% APPLIED, CENTURA |

FIG. 26O

| | | | | | |
|---|---|---|---|---|---|
| 79 | e-ZMW | Al + TiN deposition | Dep Thk | 100/30 | 10% | nm | AMAT ENDURA |
| 80 | e-ZMW | Clearout Litho | Opens Al/TiN over WGAM | | | | I-Line Litho |
| 81 | e-ZMW | TiN/Al etch | No remaining metal | 130 | OE | nm | LAM ALLIANCE |
| 82 | e-ZMW | FCOPEN Litho | Opening CD | 2 | 10% | um | I-Line Litho |
| 83 | e-ZMW | BARC etch | No remaining oxide | | OE | nm | LAM ALLIANCE |
| 84 | e-ZMW | TiN/Al etch | No remaining metal | 130 | OE | nm | LAM ALLIANCE |
| | e-ZMW | Clean backside | | | | | |
| 85 | e-ZMW | PECVD oxide HM dep | Dep Thk | 50 | 10% | nm | APPLIED, CENTURA |
| 86 | e-ZMW | eZMW litho | ZMW Hole CD | 210 | 10% | nm | 193nm Litho |
| 87 | e-ZMW | BARC + oxide etch | No remaining oxide | 50 | OE | nm | LAM ALLIANCE |
| 88 | e-ZMW | TiN/Al etch | No remaining metal | 130 | OE | nm | LAM ALLIANCE |
| 89 | e-ZMW | eZMW etch | eZMW oxide Depth | 150 | 10% | nm | LAM ALLIANCE |
| | e-ZMW | CD measurement | eZMW diameter (Al/Oxide interface) | 150 | 10% | nm | |
| | e-ZMW | Defect inspection | | | | | |
| 90 | e-ZMW | Al2O3 dep | Dep Thk | 10 | 10% | nm | ALD POLYGON |
| 91 | e-ZMW | Al2O3 etch | No Al2O3 at eZMW bottom | 10 | OE | nm | LAM TCP 9400 |

FIG. 26Q

ARRAYS OF INTEGRATED ANALYTICAL DEVICES

CROSS-REFERENCE TO RELATED APPLICATIONS

This application is a continuation of U.S. patent application Ser. No. 14/836,629, filed Aug. 26, 2015, and claims the benefit under 35 U.S.C. § 119(e) of U.S. Provisional Application No. 62/042,793, filed on Aug. 27, 2014, the disclosures of which are incorporated herein by reference in their entireties.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it can require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex.

At the same time, there is a continuing need to increase the performance of analytical systems and reduce the cost associated with manufacturing and using the system. In particular, there is a continuing need to increase the throughput of analytical systems. There is a continuing need to reduce the size and complexity of analytical systems. There is a continuing need for analytical systems that have flexible configurations and are easily scalable.

SUMMARY OF THE INVENTION

The instant invention addresses these and other problems by providing in one aspect an array of integrated analytical devices, each device comprising:

a nanoscale emission volume;
a detector layer optically coupled to the nanoscale emission volume;
a diffractive beam shaping element disposed between the nanoscale emission volume and the detector layer; and
a color filtration layer disposed between the diffractive beam shaping element and the detector layer;
wherein light is emitted from the nanoscale emission volume by a plurality of emitters within the emission volume;
wherein the detector layer comprises a plurality of sensing regions; and
wherein the diffractive beam shaping element spatially separates the light emitted from the nanoscale emission volume and directs the spatially-separated light through the color filtration layer to the plurality of sensing regions.

In another aspect, the invention provides an array of integrated analytical devices, each device comprising:

a nanoscale emission volume;
a detector layer optically coupled to the nanoscale emission volume;
a diffractive beam shaping element disposed between the nanoscale emission volume and the detector layer; and
a color filtration layer disposed between the diffractive beam shaping element and the detector layer, wherein the color filtration layer comprises 2 to 9 color filtration elements, each color filtration element specific for a range of light wavelengths;
wherein light is emitted from the nanoscale emission volume by a plurality of emitters within the emission volume;
wherein the detector layer comprises a plurality of sensing regions, and wherein the sensing regions are optically coupled to the color filtration elements; and
wherein the diffractive beam shaping element spatially separates the light emitted from the nanoscale emission volume into a plurality of beams and directs the spatially-separated light beams through the color filtration elements and onto the sensing regions.

In some embodiments, the above arrays further comprise an analyte disposed within the nanoscale emission volume. In specific embodiments, the analyte comprises a biological sample, in more specific embodiments the biological sample comprises a nucleic acid, and in even more specific embodiments the biological sample comprises a polymerase enzyme.

The above arrays can comprise at least 1,000, at least 10,000, at least 100,000, at least 1,000,000, or even at least 10,000,000 nanoscale emission volumes.

In another aspect, the invention provides methods for producing the arrays of integrated analytical devices disclosed herein.

BRIEF DESCRIPTION OF THE DRAWINGS

FIGS. 7A-7B illustrate two views of a simplified integrated analytical device including a diffractive beam shaping element for the spacial separation of emitted light.

FIGS. 8A-8C illustrate the effects of modification of the diffractive beam shaping element design on, for example, the spacing between the diffractive beam shaping element and the detector layer.

FIGS. 16A-16B illustrate the physical properties of an exemplary dielectric stack and the relationship between the number of stack layers and optical transmission.

FIGS. 20A-20D illustrate the layouts of integrated devices within exemplary arrays of the disclosure.

DETAILED DESCRIPTION OF THE INVENTION

Integrated Analytical Devices

Figure 1A:
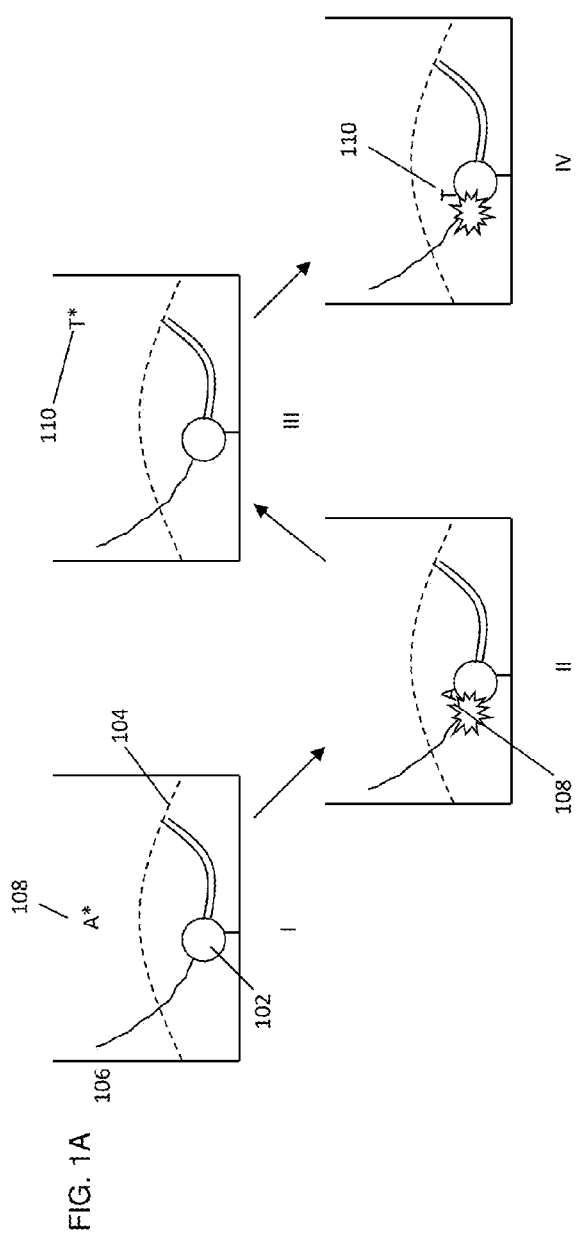
FIGS. 1A-1B schematically illustrate an exemplary nucleic acid sequencing process that can be carried out using the disclosed arrays of integrated analytical devices.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the devices and systems described herein are of broader application.

In the context of single molecule nucleic acid sequencing analyses, a single immobilized nucleic acid synthesis complex, comprising a polymerase enzyme, a template nucleic acid, whose sequence one is attempting to elucidate, and a primer sequence that is complementary to a portion of the template sequence, is observed to identify individual nucleotides as they are incorporated into the extended primer sequence. Incorporation is typically monitored by observing an optically detectable label on the nucleotide, prior to, during or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases can be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but the nucleotides are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase-mediated template dependent primer extension reaction is monitored as it occurs. In preferred aspects, the template/polymerase primer complex is provided, typically immobilized, within an optically confined region, such as a zero mode waveguide (ZMW), or proximal to the surface of a transparent substrate, optical waveguide, or the like (see e.g., U.S. Pat. Nos. 6,917,726, and 7,170,050 and U.S. Patent Application Publication No. 2007/0134128, the full disclosures of which are hereby incorporated by reference herein in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. Although the analyte of interest in the devices disclosed herein is a template/polymerase primer complex that is incorporating fluorescently-labeled nucleotides, it should be understood that other analytes of interest, in particular fluorescent analytes of interest, can be monitored using the devices of the instant disclosure.

Figure 1B:
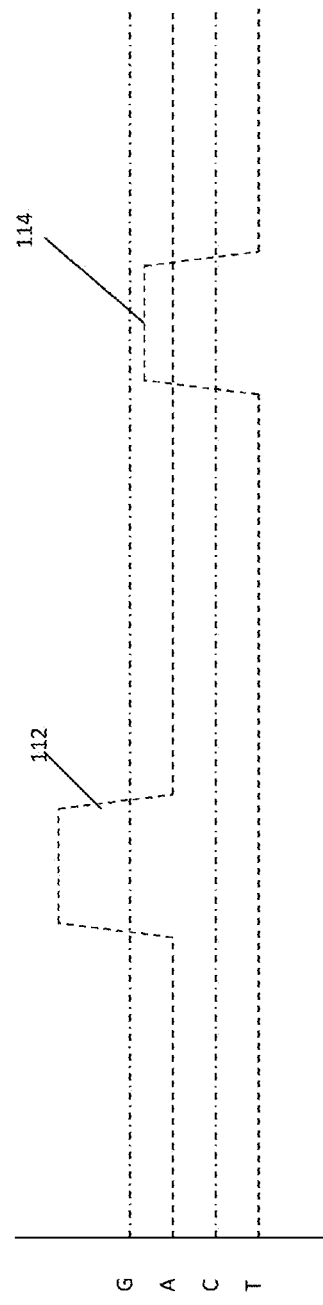

A schematic illustration of this sequencing process is shown in FIGS. 1A-1B. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation which produces a signal associated with that retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

The above sequencing reaction can be incorporated into a device, typically an integrated analytical device, that provides for the simultaneous observation of multiple sequencing reactions, ideally in real time. While the components of each device and the configuration of the devices in the system can vary, each integrated analytical device typically comprises, at least in part, the general structure shown as a block diagram in FIG. 2. As shown, an integrated analytical device 200 typically includes a reaction cell 202, in which the analyte (i.e., the polymerase-template complex and associated fluorescent reactants) is disposed and from which the optical signals emanate. The analysis system further includes a detector element 220, which is disposed in optical communication with the reaction cell 202. Optical communication between the reaction cell 202 and the detector element 220 is provided by an optical train 204 comprised of one or more optical elements generally designated 206, 208, 210 and 212 for efficiently directing the signal from the reaction cell 202 to the detector 220. These optical elements generally comprise any number of elements, such as lenses, filters, gratings, mirrors, prisms, refractive material, apertures, or the like, or various combinations of these, depending upon the specifics of the application. By integrating these elements into a single device architecture, the efficiency of the optical coupling between the reaction cell and the detector is improved. Examples of integrated analytical systems, including various approaches for illuminating the reaction cell and detecting optical signals emitted from the reaction cell, are described in U.S. Patent Application Publication Nos. 2012/0014837, 2012/0019828, and 2012/0021525, which are each incorporated by reference herein in their entireties for all purposes.

Figure 2:
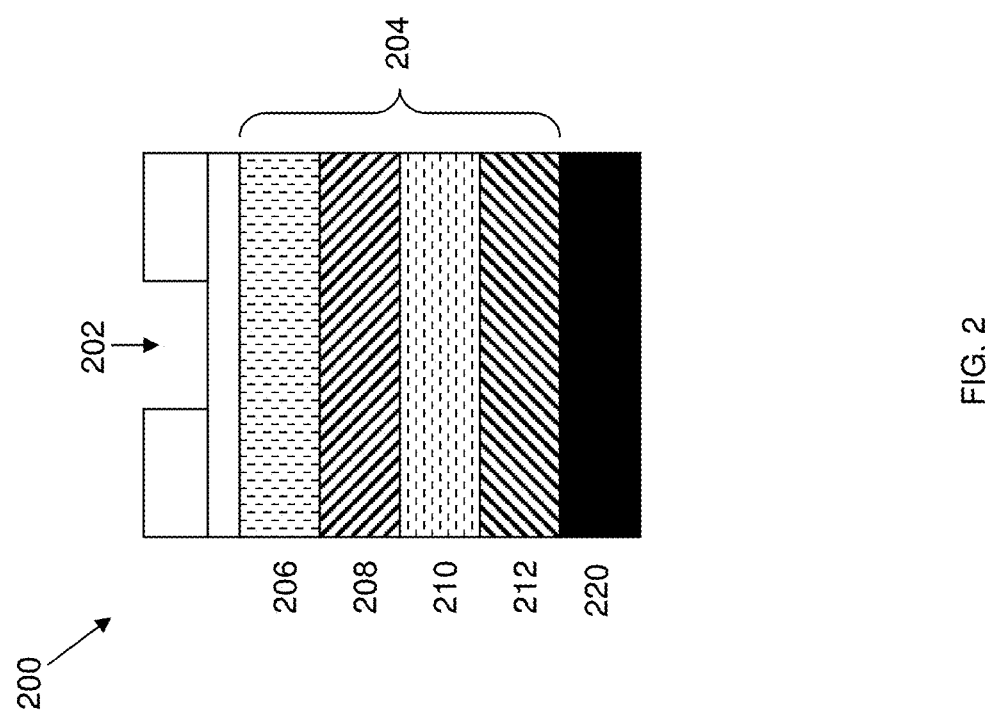
FIG. 2 provides a schematic block diagram of an integrated analytical device.

As noted above, an analyte (e.g., a polymerase-template complex with associated fluorescent reactants) disposed within a reaction cell (e.g., element 202 in FIG. 2) or otherwise immobilized on the surface of the device, emits light that is transmitted to a detector element (e.g., element 220 in FIG. 2). For fluorescent analytes, the analyte is illuminated by an excitation light source, whereas for other analytes, such as chemiluminescent or other such analytes, an excitation light source may not be necessary. At least a portion of the reaction cell volume, the emission volume, is optically coupled to the detector element, so that light emitted from an analyte within this volume is measured by the detector element. In order to maximize the number of analytes measured simultaneously, the size of the instant analytical devices are reduced as much as possible, so that the emission volume within each device is a nanoscale emission volume. Ideally, the optical coupling between the nanoscale emission volume and the detector element is highly efficient, in order to maximize the sensitivity of the device and maximize the signal output. As described in further detail below, light emitted from the nanoscale emission volume can be further manipulated, for example by lens elements and color filtration layers, prior to reaching the detector element.

Conventional analytical systems typically measure multiple spectrally distinct signals or signal events and must therefore utilize complex optical systems to separate and distinctly detect those different signal events. The optical path of an integrated device can be simplified, however, by a reduction in the amount or number of spectrally distinguishable signals that are detected. Such a reduction is ideally effected, however, without reducing the number of distinct reaction events that can be detected. For example, in an analytical system that distinguishes four different reactions based upon four different detectable signal events, where a typical system would assign a different signal spectrum to each different reaction, and thereby detect and distinguish each signal event, in an alternative approach, four different signal events would be represented by fewer than four different signal spectra, and would, instead, rely, at least in part, on other non-spectral distinctions between the signal events.

For example, a sequencing operation that would conventionally employ four spectrally distinguishable signals, e.g., a "four-color" sequencing system, in order to identify and characterize the incorporation of each of the four different nucleotides, could, in the context of an alternative configuration, employ a one-color or two-color analysis, e.g., relying upon a signals having only one or two distinct or distinguished spectral signals. However, in such an alternative configuration, this reduction in reliance on signal spectral complexity does not come at the expense of the ability to distinguish signals from multiple, i.e., a larger number of different signal producing reaction events. In particular, instead of relying solely on signal spectrum to distinguish reaction events, such an alternative configuration can rely upon one or more signal characteristics other than emission spectrum, including, for example, signal intensity, excitation spectrum, or both, to distinguish signal events from each other.

In one particular alternative configuration, the optical paths in an integrated analytical device can thus be simplified by utilizing signal intensity as a distinguishing feature between two or more signal events. In its simplest iteration, and with reference to an exemplary sequencing process, two different types of nucleotides would bear fluorescent labels that each emit fluorescence under the same excitation illumination, i.e., having the same or substantially overlapping spectral band, and thus would provide benefits of being excited using a single excitation source. The resulting signals from each fluorescent label would have distinct signal intensities or amplitudes under that same illumination, and would therefore be distinguishable by their respective signal amplitudes. These two signals could have partially or entirely overlapping emission spectra, but separation of the signals based upon any difference in emission spectrum would be unnecessary.

Accordingly, for analytical systems using two or more signal events that differ in signal amplitude, the integrated analytical devices of such systems can readily benefit through the removal of some or all of those components that would normally be used to separate spectrally distinct signals, such as multiple excitation sources and their associated optical trains, as well as the color separation optics, e.g., filters and dichroics, for the signal events, which in many cases, requires at least partially separate optical trains and detectors for each spectrally distinct signal. As a result, the optical paths for these integrated analytical devices are greatly simplified, allowing placement of detector elements in closer proximity to reaction cells, and improving overall performance of the detection process for these devices.

Figure 3:
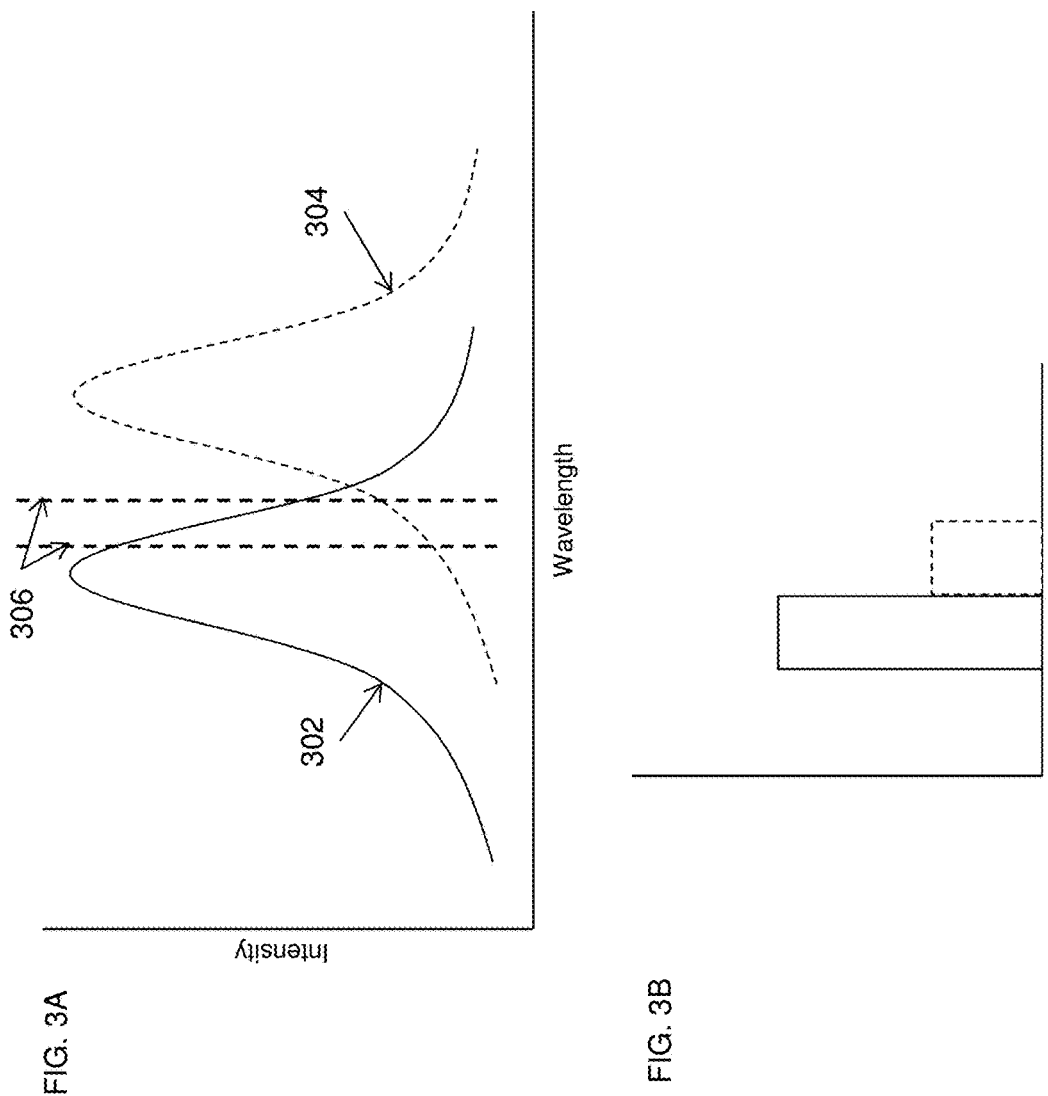
FIG. 3A provides a schematic of excitation spectra for two signal events and an indicated narrow band excitation illumination, while FIG. 3B schematically illustrates the resulting detected signal based upon the narrow band illumination of the two signal events.

Provision of a signal-producing analyte that will produce different signal amplitudes under a particular excitation illumination profile can be accomplished in a number of ways. For example, different fluorescent labels can be used that present excitation spectral profiles that overlap but include different maxima. As such, excitation at a narrow wavelength will typically give rise to differing signal intensities for each fluorescent group. This is illustrated in FIG. 3A, which shows the excitation spectra of two different fluorescent label groups (solid and dashed lines 302 and 304, respectively). When subjected to excitation illumination at the wavelength range shown by vertical lines 306, each fluorescent label will emit a signal at the corresponding amplitude. The resulting signal intensities at a given excitation wavelength are then shown in the bar chart of FIG. 3B as solid lined and dashed lined bars, respectively. The difference in intensity of these two signal producing labels at the given excitation wavelength is readily used to distinguish the two signal events. As will be appreciated, such spectrally indistinct signals would not be easily distinguishable when occurring simultaneously, as they would result in an additive overlapping signal, unless, as discussed below, such spectrally indistinct signals result from spectrally distinct excitation wavelengths. As will be appreciated, this same approach can be used with more than two label groups, where the resulting emission at a given excitation spectrum have distinguishable intensities or amplitudes.

Similarly, two different fluorescent labeling groups can have the same or substantially similar excitation spectra, but provide different and distinguishable signal emission intensities due to the quantum yield of those labeling groups.

Further, although described in terms of two distinct fluorescent dyes, it will be appreciated that each different labeling group can each include multiple labeling molecules. For example, each reactant can include an energy transfer dye pair that yields emissions of differing intensities upon excitation with a single illumination source. For example, a labeling group can include a donor fluorophore that is excited at a given excitation wavelength, and an acceptor fluorophore that is excited at the emission wavelength of the donor, resulting in energy transfer to the acceptor. By using different acceptors, whose excitation spectra overlap the emission spectrum of the donor to differing degrees, such an approach can produce overall labeling groups that emit at different signal amplitudes for a given excitation wavelength and level. Likewise, adjusting the energy transfer efficiency between the donor and acceptor will likewise result in differing signal intensities at a given excitation illumination.

Alternatively, different signal amplitudes can be provided by different multiples of signal producing label groups on a given reactant, e.g., putting a single label molecule on one reactant while putting 2, 3, 4, or more individual label molecules on a different reactant. The resulting emitted signal will be reflective of the number of labels present on a reactant and thus will be indicative of the identity of that reactant.

Exemplary compositions and methods relating to fluorescent reagents, such as nucleotide analogs, useful for the above purposes are described in, for example, U.S. Patent Application Publication Nos. 2012/0058473; 2012/0077189; 2012/0052506; 2012/0058469; 2012/0058482; 2010/0255488; 2009/0208957, which is each incorporated by reference herein in its entirety for all purposes.

As described above, integrated analytical devices making use of such approaches see a reduction in complexity by elimination of spectral discrimination requirements, e.g., using signal amplitude or other non-spectral characteristics as a basis for signal discrimination. Integrated analytical devices that combine such non-spectral discrimination approaches with the more common spectral discrimination approaches can also provide advantages over more complex spectral discrimination systems. By shifting from a "four-color" discrimination system to a system that distinguishes signals based upon signal intensity and color, one can still reduce the complexity of the overall optical system relative to a conventional four-color separation scheme. For example, in an analytical operation that detects four discrete reaction events, e.g., in a nucleic acid sequencing analysis, two signal events can be provided within a given emission/detection spectrum, i.e., emitting signals within the same spectral window, and the other two events within a distinct emission/detection spectrum. Within each spectral window, the pair of signal events produce distinguishable signal intensities relative to each other.

For ease of discussion, this concept is described in terms of two groups of fluorescent signal events, where members of each group differ by fluorescent intensity, and the groups differ by virtue of their emission spectrum. As will be appreciated, the use of simplified optics systems, e.g., using two detection channels for two distinct emission spectra, does not require that the emission profiles of the two groups of signals do not overlap or that the emission spectra of members of each group perfectly overlap. Instead, in many preferred aspects, more complex signal profiles can be used where each different signal event possesses a unique emission spectrum, but in a way that each signal will present a signal profile within the two detection channels that is unique, based upon the signal intensity in each channel.

For use in the instant devices, each "emitter" in a sample should thus have a unique signal profile, as just described, in order to be properly identified. Samples containing a plurality of emitters can thus be readily distinguished using the instant devices. In some embodiments, the devices distinguish 4 to 18 emitters 4 to 12 emitters, or even 4 to 8 emitters. In specific embodiments, the devices distinguish four emitters, for example the four different bases of the nucleic acid sequencing reaction.

Figure 4:
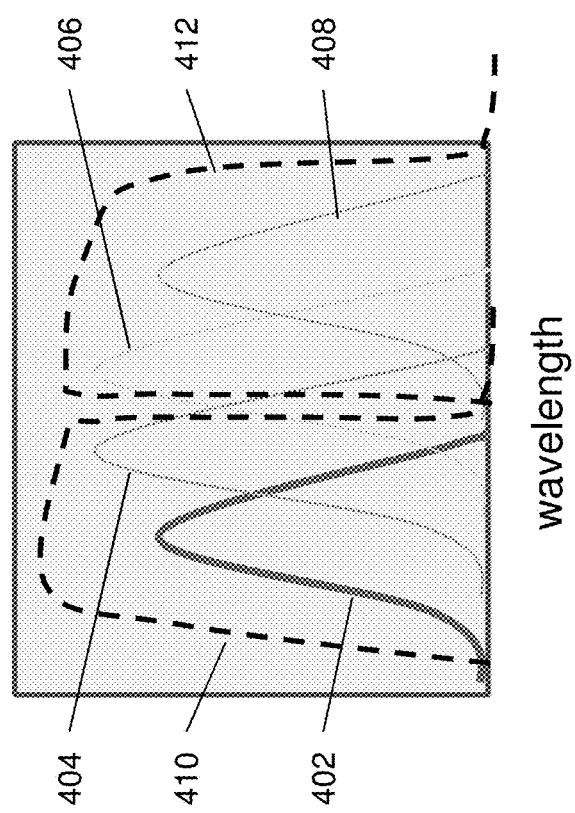
FIG. 4 schematically illustrates the signal profiles for each of four fluorescent labeling groups, overlain with each of two different color filter profiles.

FIG. 4 schematically illustrates the signal profiles for each of four fluorescent labeling groups, overlain with each of two different filter profiles. As shown, four label groups yield emission spectra 402, 404, 406, and 408, respectively. While the signals from these four groups partially overlap each other, they each have different maxima. When subjected to a two channel filter scheme, as shown by pass filter lines 410 and 412, the signal from each label will produce a unique signal profile between the two detection channels. In particular, signals are routed through an optical train that includes two paths that are filtered according to the spectral profile shown. For each signal, different levels of emitted light will pass through each path and be detected upon an associated detector. The amount of signal that passes through each filter path is dictated by the spectral characteristics of the signal.

In the case of the above described mixed-mode schemes, detection systems can be provided that include at least two distinct detection channels, where each detection channel passes light within a spectrum that is different from each other channel. Such systems also include a reaction mixture within optical communication of the detection channels, where the reaction mixture produces at least three different optical signals that each produces a unique signal pattern within the two detection channels, as compared to the other optical signals.

In all cases, each signal-producing reactant is selected to provide a signal that is entirely distinct from each other signal in at least one of signal intensity and signal channel. As noted above, signal intensity in a given channel is dictated, in part, by the nature of the optical signal, e.g., its emission spectrum, as well as the filters through which that signal is passed, e.g., the portion of that spectrum that is allowed to reach the detector in a given channel. However, signal intensity can also be modulated by random variables, such as orientation of a label group when it is emitting signal, or other variables of the particular reaction. Accordingly, for a signal's intensity to be assured of being entirely different from the intensity of another signal within a given channel, in preferred aspects, this variation is accounted for.

Figure 5:
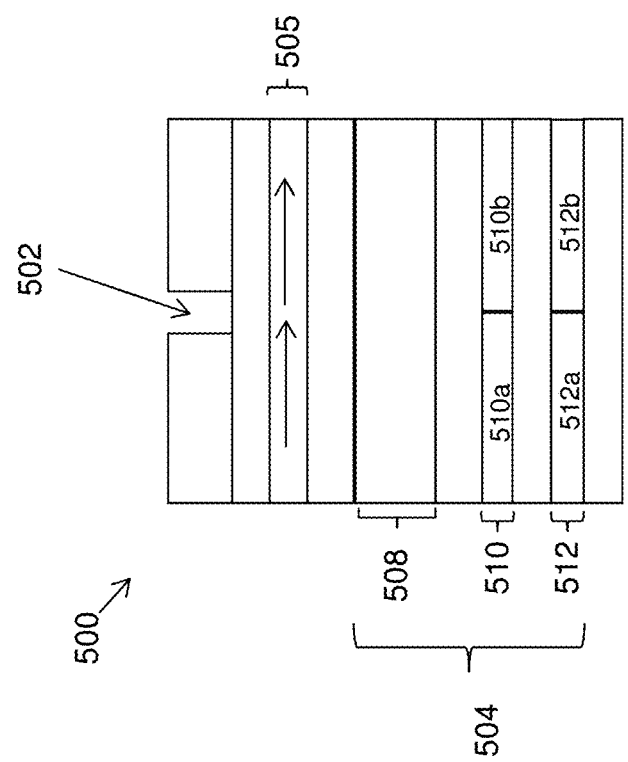
FIG. 5 schematically illustrates an integrated analytical device for detecting signals from a sequencing reaction, where a lens element spatially separates light emitted from a reaction cell, and directs the light through a color filtration layer and onto a detector layer.

With a reduced number of spectrally distinct signal events, the complexity of the optical paths for the integrated devices is also reduced. FIG. 5 illustrates a not-to-scale example device architecture for performing optical analyses, e.g., nucleic acid sequencing processes, that rely in part on non-spectral discrimination of differing signals, and optionally, in part on spectral distinction. As shown, an integrated analytical device 500 can include a reaction cell 502 that is defined upon the surface layer of the device. As shown in this drawing, the reaction cell comprises a nanowell disposed in the surface layer. Such nanowells can constitute depressions in a substrate surface or apertures disposed through additional substrate layers to an underlying transparent substrate, e.g., as used in zero mode waveguide (ZMW) arrays (see, e.g., U.S. Pat. Nos. 7,181,122 and 7,907,800, and also below). It should also be understood, however, that in some embodiments, the sample of interest can be confined in other ways, and that the nanoscale reaction cell in those embodiments can be omitted from the analytical devices. For example, if a target of interest is immobilized in a pattern on the surface of a device lacking separate reaction cells, binding events, or other events of interest, could be observed at those locations without the need for physical separation of the samples. Hybridization reactions, for example between immobilized nucleic acids and their complimentary sequences, or binding reactions, for example between antibodies and their ligands, where either member of the binding pair can be immobilized at a particular location on the surface of the device, could suitably be monitored using such an approach, as would be understood by those of ordinary skill in the art.

Excitation illumination is delivered to the reaction cell or to the immobilized target from an excitation light source (not shown) that can be separate from or also integrated into the substrate. As shown, an optical waveguide (or waveguide layer) 505 can be used to convey excitation light (shown by arrows in one direction, although light can be propagated in either direction or both directions, as desired) to the reaction cell 502 or otherwise immobilized target, where the evanescent field emanating from the waveguide 505 illuminates reactants within the illumination volume. Use of optical waveguides to illuminate reaction cells is described in e.g., U.S. Pat. No. 7,820,983 and U.S. Patent Application Publication No. 2012/0085894, which are each incorporated by reference herein in their entireties for all purposes. The nanoscale reaction cell (also referred to herein as the "nanowell" or "ZMW") can act to enhance the emission of fluorescence downward into the device and limit the amount of light scattered upwards.

The emitted light, whether from a nanoscale reaction cell or from an immobilized target, is directed to the detector through an integrated optical train 504 comprising one or more optical elements. The optical train includes a lens element layer 508 to direct emitted light from an emission volume within the reaction cell to a detector layer 512 disposed beneath the reaction cell. As described in more detail below, the lens element layer in the integrated analytical devices of the instant disclosure preferably comprises a diffractive beam shaping element that serves to separate at high efficiency the emitted light into at least two beams for passage through the color filtration layer 510. The diffractive beam shaping element may, for example, separate the emitted light into two, three, four, or even more at least partially separated beams directed onto the detector layer. Depending on the configuration of the diffractive beam shaping element, the split beams can be organized in a linear fashion, or they can be arranged in an array, for example in a 2×2 beam array or the like. Such arrangements will typically be dictated by the configuration of the sensing regions of the detector layer.

The detector layer typically comprises one, or preferably multiple, sensing regions 512a-b, e.g., pixels in an array detector, for example a CMOS detector, that are optically coupled through the diffractive beam shaping element to an emission volume within a given analytical device. Although illustrated as a linear arrangement of pixels 512a-b, it will be appreciated that such pixels can be arranged in a grid, n×n square, n×m rectangle, annular array, or any other convenient orientation. Exemplary arrangements are described in more detail below.

It should be understood in the context of the disclosure that the "optical coupling" of two components in a device is not intended to imply a directionality to the coupling. In other words, since the transmission of optical energy through an optical device is fully reversible, the optical coupling of a first component to a second component should be considered equivalent to the optical coupling of the second component to the first component.

Emitted signals from the reaction cell 502 that impinge on the pixels of the detector layer are then detected and recorded. As noted above, a color filtration layer 510 is preferably disposed between the detector layer and the nanoscale emission volume, to permit different spectrally distinct signals to travel to different associated sensing regions 512a and 512b in the detector layer 512. For example, the portion 510a of filter layer 510 allows only signals having a distinct first emission spectrum to reach its associated sensing region 512a, while filter portion 510b of filter layer 510 allows only signals having a distinct second spectrum to reach its associated sensing region 512b.

In the context of a sequencing system exploiting such a configuration, incorporation of two of the four nucleotides would produce signals that would be passed through filter portion 510a to sensing region 512a, and blocked by filter portion 510b. As between these two signals, one signal would have a signal intensity higher than the other, such that the sensing region 512a in detector layer 512 would be able to produce signal responses indicative of such differing signal intensities. Likewise, incorporation of the other two of the four nucleotides would produce signals that would be passed through filter portion 510b to sensing region 512b, and blocked by filter portion 510a. As between these two signals, one signal would have a signal intensity higher than the other, such that the sensing region 512b in detector layer 512 would be able to produce signal responses indicative of such differing signal intensities.

The detector layer is operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Patent Application Publication No. 2012/0019828.

As will be appreciated from the foregoing disclosure and FIG. 5, the integrated analytical devices described herein do not require the more complicated optical paths that are necessary in systems utilizing conventional four-color optics, obviating in some cases the need for excessive signal separation optics, dichroics, prisms, or filter layers. In particular, although shown with a single filtration layer, as noted, in optional aspects, the filtration layer could be eliminated or could be replaced with a filtration layer that blocks stray light from the excitation source, e.g., a laser rejection filter layer (see below), rather than distinguishing different emission signals from the reaction cell. Even including the filtration layer 510, results in simplified and/or more efficient optics as compared to conventional four-color systems, which require either multilayer filters, or narrow band pass filters, which typically require hybrid layers or composite approaches over each subset of sensing regions, thus blocking signal from reaching one or more of the sensing region subsets at any given emission wavelength, resulting in the detection of far fewer photons from each signal event. The optics configuration shown in FIG. 5, on the other hand, only blocks a smaller portion of the overall signal light from reaching the detector. Alternatively, such conventional systems would require separation and differential direction of all four different signal types, resulting in the inclusion of additional optical elements, e.g., prisms or gratings, to achieve spectral separation. Examples of nanoscale integrated analytical devices that include spectral diversion elements (i.e., optical elements that spatially separate light based on color) are provided in U.S. Patent Application Publication No. 2012/0021525.

Figure 6:
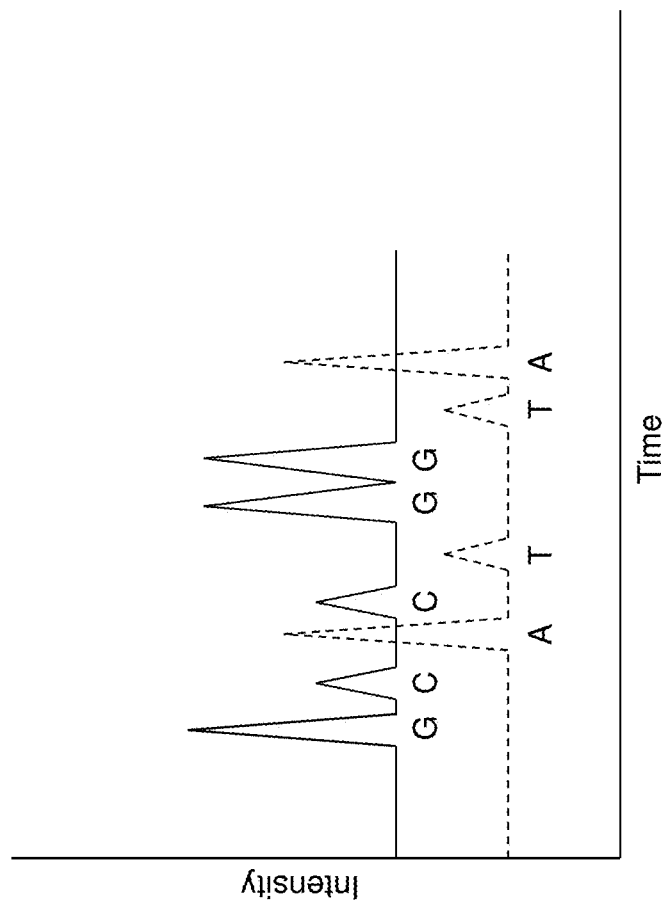
FIG. 6 schematically illustrates signal traces for a two-color, two-amplitude sequence-by-synthesis reaction.

FIG. 6 shows a schematic exemplar signal output for a real time sequencing operation using a two color/two amplitude signal set from an integrated system of the invention where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

Lens Elements for Spatial Separation of Emitted Light

As mentioned above, the nanoscale integrated analytical devices of the instant disclosure include a lens element layer disposed between the nanoscale emission volume and the detector layer. The lens elements of such a layer serve to direct light emitted from the nanoscale emission volume along two or more spatially separated optical paths at high efficiency. In addition to splitting the emitted optical signals into separate optical paths, the lens element can additionally collimate and/or focus the emitted light. In particular, such lens elements are ideally capable of collimating emitted light with near on-axis rays, as well as splitting the emitted light, for example prior to color separation by the color filtration layer. In addition, such lens elements are readily fabricated using standard techniques.

The integrated optical lens elements of the instant devices can be either refractive lenses or diffractive lenses, depending on the optical and physical properties desired, as would be understood by those of ordinary skill in the art. A diffractive lens may, in some circumstances, provide improved image quality, be more easily miniaturized, and/or be less expensive to fabricate than a comparable refractive lens. In some cases, the lenses can include separate refractive and diffractive components or can be hybrid lenses that combine both features in a single lens element.

In preferred embodiments, the lens element of the instant analytical devices is a diffractive beam shaping element or a variant thereof. Such elements typically include Fresnel-like lens features. Fresnel lenses, which are also known as zone plates or Fresnel zone plates when they function by diffraction rather than refraction or reflection, consist of a series of concentric rings with a specific tapered shape, or with alternating transparent and opaque zones (also called the Fresnel zones), with respect to the incident irradiation. These structures result in the focusing of light passing through the device by selective absorption or selective phase shifting and thus allow the device to function as a lens. The specific lens design depends on the radiation to be focused, the refractive index of the material used to construct the lens, and the desired focal length, as is well known in the art. In some embodiments, the lens element of the instant devices is a modified Fresnel lens that functions as a diffractive array focusing element. This hybrid lens element can be referred to as a diffractive beam shaping element due to its ability to spatially separate emitted light into a plurality of spots. While the integrated analytical devices of the instant disclosure will be described in various embodiments as including a diffractive beam shaping element, it should be understood that these are preferred embodiments of the devices, and that other lens elements can be included in the instant analytical devices without limitation.

A variety of materials and methods can be used to fabricate the lens elements of the instant devices, as would be understood by those of ordinary skill in the art. For example, the lens elements can be formed by the etching of zones in the planar surface of a material transparent to the light of interest and the subsequent deposition of an absorbing or phase shifting material into the etched zones. For example, a phase Fresnel zone plate is a staircase approximation to a phase Fresnel lens. The efficiency of the phase Fresnel zone plate increases as the number of levels is increased. Specifically, a two-phase Fresnel zone plate can be shown to have a maximum diffraction efficiency of 40.5%, whereas a four-phase Fresnel zone plate has a maximum diffraction efficiency of 81%. The optical efficiency of the lens element, such as a diffractive beam shaping element, is therefore in some embodiments at least 40%, at least 50%, at least 60%, at least 70%, at least 80%, or even higher. In preferred embodiments, the optical efficiency is at least 40%. Techniques for designing a lens element with the desired spatial separation capabilities are known in the art. For example, the application of binary-optics technology in the design of optical elements for the manipulation of laser beams (e.g., for splitting and combining laser beams) is described by Leger et al. (1988) The Lincoln Laboratory Journal 1(2): 225. Optical ray tracing software, such as the optical design program Zemax, can be used to design such elements.

Fresnel lenses, and variants thereof, have been incorporated into advanced optical devices using various techniques, for example as imaging optics in illumination systems (see, e.g., U.S. Pat. No. 6,002,520), in light emitting devices (see, e.g., U.S. Pat. No. 6,987,613), in solid-state imaging devices (see, e.g, U.S. Pat. No. 7,499,094), in image sensors (see, e.g., U.S. Pat. No. 8,411,375), and in integrated infrared sensors (see, e.g., U.S. Patent Application Publication No. 2013/0043552). The design of the lens elements of the instant disclosure and their integration into the instant analytical device arrays can be achieved using analogous approaches.

The use of a diffractive beam shaping element for spatial separation of light in the detection pathway of the instant devices provides several advantages over traditional optical elements, such as reflective cones or parabolic mirrors. In particular, such diffractive beam shaping elements provide off-axis focusing of light emitted from an emission volume. Such elements further require minimal area, minimal pitch, and result in minimal crosstalk between adjacent detector elements. Unlike reflective cones or parabolic mirrors, as typically used in nanoscale integrated analytical devices, or traditional refractive lens elements, the diffractive beam shaping elements of the instant disclosure can simultaneously collimate and split light emitted from an emission volume at high efficiency. Furthermore, the instant diffractive beam shaping elements are readily manufactured using standard microchip fabrication techniques, for example using standard deposition, removal, and patterning techniques.

Two views of a simplified exemplary integrated analytical device that includes a diffractive beam shaping element for spatial separation of emitted light are shown in FIGS. 7A-7B. FIG. 7A shows a top-down view of a two-pixel device (i.e., a device containing two sensing regions in the detector layer), where the ZMW/nanowell 702 is positioned above the border between the two sensing regions, 712a and 712b. It should be noted that the intervening diffractive beam shaping element, color filtration layer, and other features of the device are omitted from the view of FIG. 7A. FIG. 7B shows a side view of the same device, indicating how light emitted from the ZMW/nanowell would pass through diffractive beam shaping element 708 and color filtration elements 710a and 710b to reach sensing regions 712a and 712b of the detector layer.

The design of the diffractive beam shaping elements of the instant devices can be varied as desired to obtain the desired spatial separation, collimation, and/or focusing of emission light passing through the element. For example, as shown in FIGS. 8A-8C, a nominal design (panel A) can include sufficient space between the diffractive beam shaping element and the detector layer to allow the inclusion of, for example, a laser rejection interference filter layer (see below) or other optical feature. In some situations, it can be advantageous to increase the lateral spacing between the diffractive beam shaping element and the detector layer (panel B), whereas in other situations, it can be advantageous to build a more compact structure, by decreasing the lateral spacing between the diffractive beam shaping element and the detector layer (panel C). The alterations in optical properties of the diffractive beam shaping element are readily achieved by modification of the design of the diffractive beam shaping element, as would be understood by those of ordinary skill in the art.

Figure 9B:
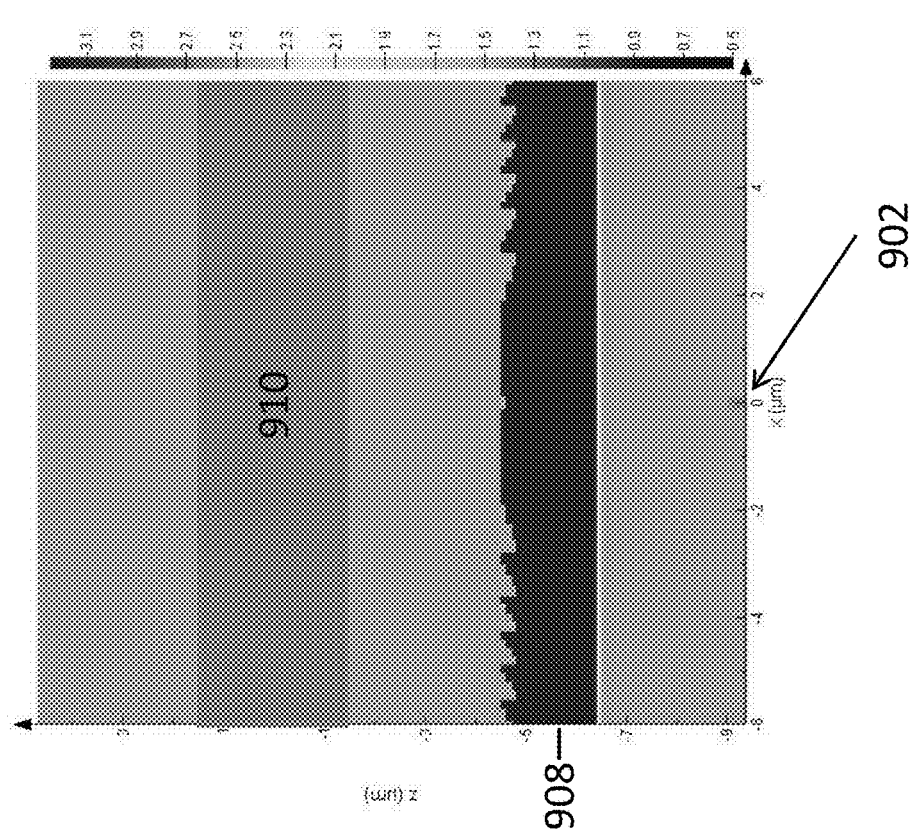
FIGS. 9A-9B represent the transmission of emission light from a ZMW/nanowell through a representative diffractive beam shaping element design.
Figure 9A:
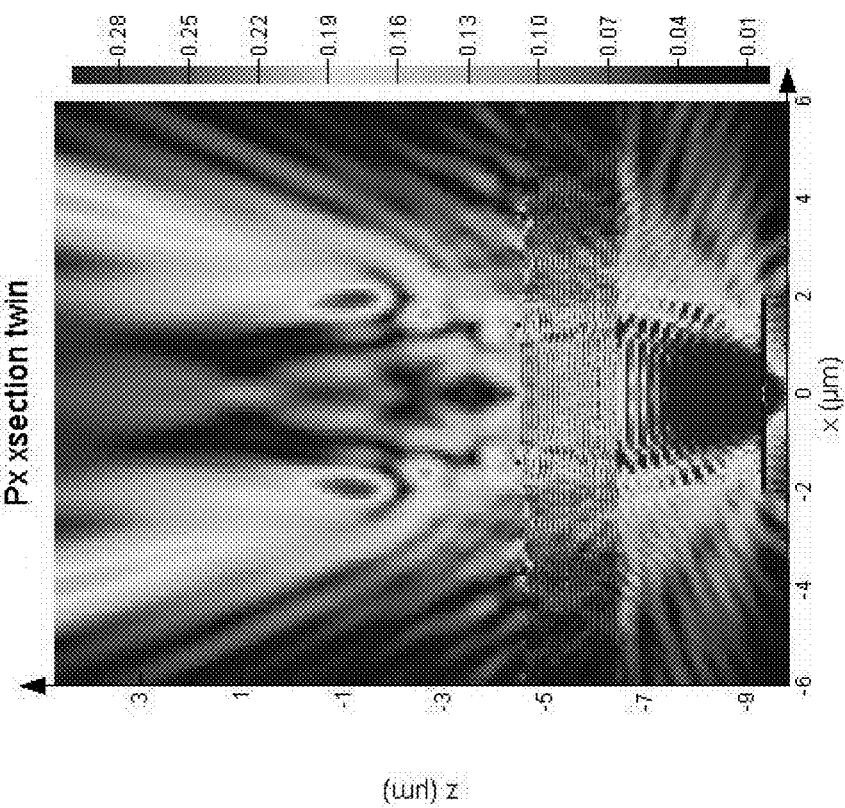

FIGS. 9A-9B demonstrate the simulated transmission of emission light from the emission volume of a ZMW/nanowell through a representative diffractive beam shaping element design. The basic design of the simulated device is shown schematically in FIG. 9A, including the positions of the ZMW/nanowell 902, the diffractive beam shaping element 908, and the color filtration layer 910. As shown in FIG. 9B, the intensity of light transmitted through a diffractive beam shaping element designed as shown in FIG. 9A is spatially separated by the diffractive effects of the diffractive beam shaping element. The composition and structure of diffractive beam shaping element 908, as shown in FIG. 9A, were designed using ZEMAX optical ray tracing software, and the transmission properties of light through the diffractive beam shaping element, as shown in FIG. 9B, were modeled using Lumerical FDTD (finite difference time domain) Maxwell equations electro-magnetic propagation software.

Figure 10B:
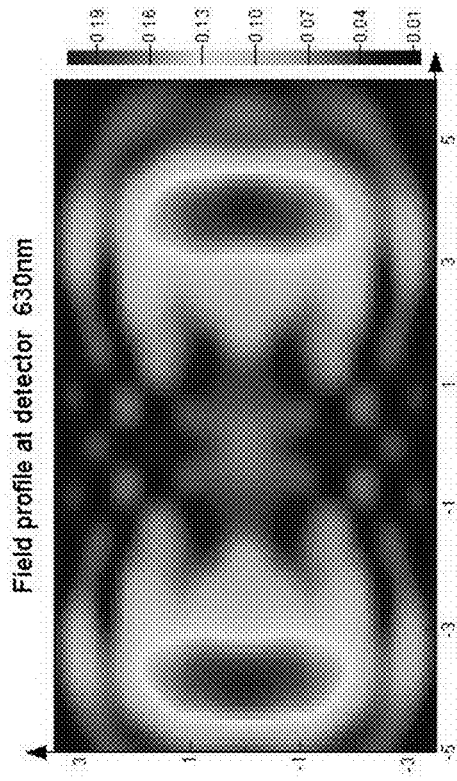
FIGS. 10A-10D illustrate the efficiency and effect of wavelength on emission passage through a twin diffractive beam shaping element in the absence of color filters.
Figure 10D:
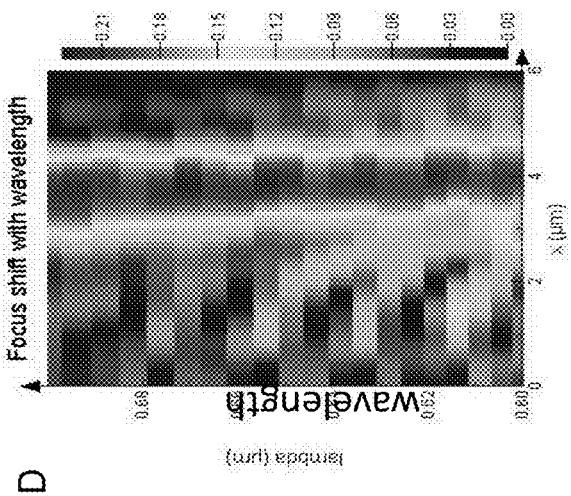
Figure 10A:
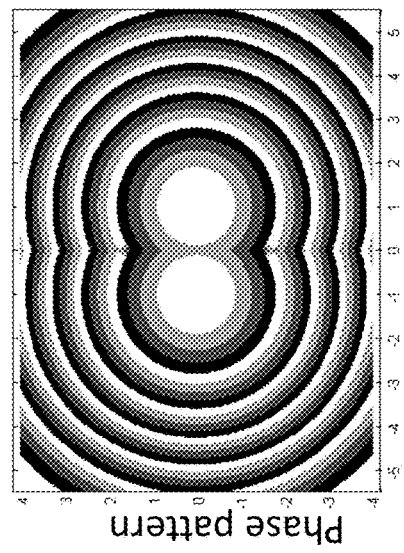
Figure 10C:
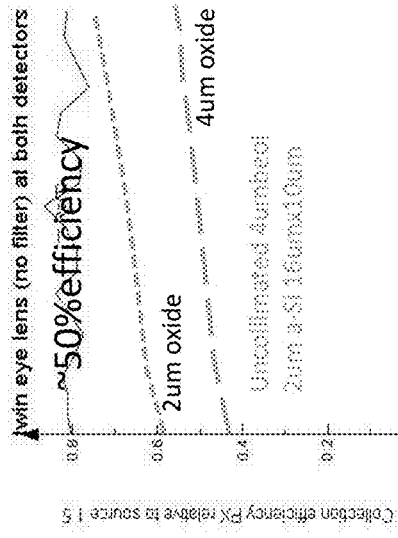

It should be noted that the instant diffractive beam shaping elements are not intended to separate light based on color. Rather, it is a feature of these diffractive beam shaping elements that they provide maximal efficiency of transmission of all spectra, and that color distinction is provided by the color filtration layer. In this regard, FIGS. 10A-10D show the efficiency and effect of wavelength on emission passage through a twin diffractive beam shaping element in the absence of color filters. The phase pattern of the diffractive beam shaping element, as viewed from above, is shown in FIG. 10A. The field profile at the detector level for a 630 nm emission is shown in FIG. 10B. The efficiency of the diffractive beam shaping element as a function of emission wavelength is shown in FIG. 10C for a collection path without any lens patterning but with the a-Si deposited. The 2 µm oxide line is for a device with the detector 2 µm away from the a-Si layer, and the 4 µm oxide line is for a device with the detector 4 µm from the a-Si layer. In these devices, the pixel is relatively large (~8 µm×10 µm). The effect of wavelength on focus of the device is shown in FIG. 10D.

Figure 11B:
FIGS. 11A-11B illustrate the design, construction, and analysis of a representative nanoscale device, including a diffractive beam shaping element for spatial separation of light transmitted from an emission volume.
Figure 11A:
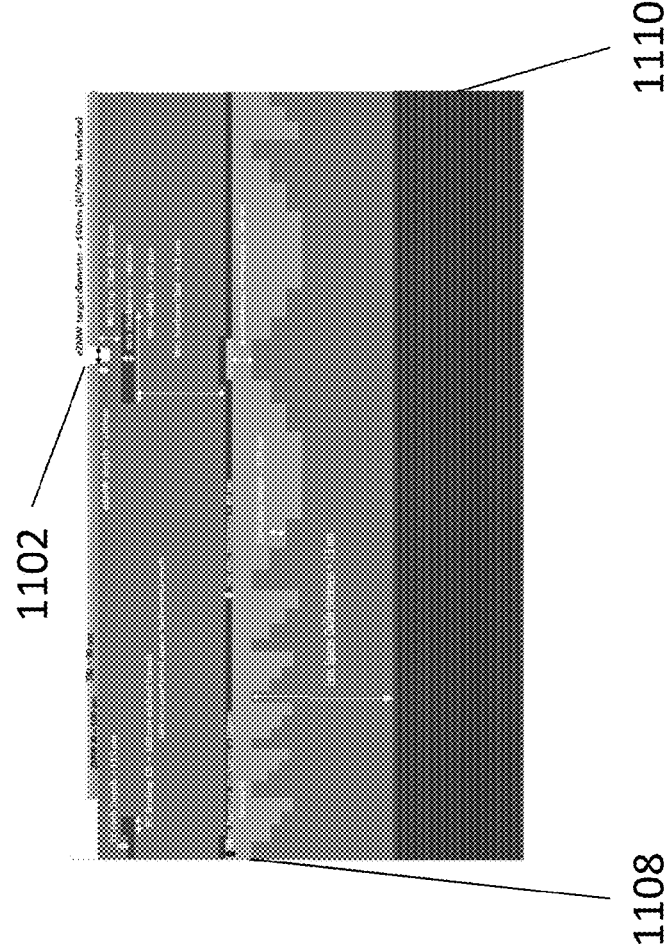

FIGS. 11A-11B illustrate the design, construction, and analysis of a nanoscale device fabricated according to the instant disclosure, including a diffractive beam shaping element for spatial separation of light transmitted from an emission volume. FIG. 11A shows the design features of the device, including the ZMW/nanowell 1102, the diffractive beam shaping element 1108, and the color filtration layer 1110. The device further includes a waveguide (WG) for delivery of excitation light to the ZMW/nanowell, metallic (Al) and antireflective (TiN) coatings on the surface of the device, silicon oxide spacer layers above and below the diffractive beam shaping element, and an aperture layer on the surface of the diffractive beam shaping element. Approximate dimensions of the various features are provided in the drawing. FIG. 11B shows an SEM micrograph corresponding to the device constructed according to the design outlined in FIG. 11A.

Aperture Layers

The integrated analytical devices of the instant disclosure can optionally include one or more aperture layers. The aperture layers are fabricated between other layers of the nanoscale analytical devices, for example between the ZMW/nanowell layer and the diffractive beam shaping element layer, between the diffractive beam shaping element layer and the color filtration layer, and/or between the color filtration layer and the detector layer. The apertures provide openings to allow maximum transmission of emitted light from the ZMW/nanowell to the sensing regions of the detector element within a given unit cell, while at the same time minimizing background transmission of light, either from the excitation source (e.g., the waveguide), from autofluorescence within the device, or from cross-talk between adjacent unit cells. Aperture layers are typically constructed of light-blocking materials where transmission of light is undesirable and of transparent materials where transmission of light is desired. Suitable light-blocking materials for use in the aperture layers include, for example, titanium nitride, metals such as chromium, or any other appropriate light-blocking material. The light-blocking material is preferably titanium nitride. Suitable transparent materials for use in the aperture layers include, for example, $SiO_2$, $Si_3N_4$, $Al_2O_3$, $TiO_2$, GaP, and the like. In preferred embodiments, the aperture layer is approximately 100 nm thick.

Laser Rejection Filter Elements and Color Filtration Elements

The integrated analytical devices of the instant disclosure additionally include features designed to transmit certain wavelengths of light, while significantly decreasing or blocking other wavelengths of light. In particular, it is desirable to transmit as much signal-related light as possible to the appropriate region of the detector, and to block all, or at least most, noise-related light. Furthermore, since the lens elements of the instant devices are designed to transmit all wavelengths of light emitted from an analyte, it is typically necessary to employ color filtration elements between the lens elements and the different sensing regions of the detector layer in order to distinguish different emitters in the analyte.

The devices therefore include a color filtration layer disposed between the lens element layer and the detector layer. A different color filtration element within the color filtration layer is typically used for each of the spatially-separated beams transmitted through the lens element. The spatially-separated light typically passes through the color filtration layer before being detected by the corresponding sensing region in the detector layer. In some embodiments of the invention, the color filtration layer comprises a plurality of color filtration elements, each color filtration element specific for a range of light wavelengths. In more specific embodiments, the color filtration layer comprises 2 to 9 color filtration elements. In even more specific embodiments, the color filtration layer comprises 2 color filtration elements, sensing regions, and separated beams.

The devices can additionally and optionally include one or more laser rejection filter elements within a laser rejection filter layer. The laser rejection filter layer is disposed between the excitation source and the detector layer, typically between the color filtration layer and the detector layer of the integrated devices. Such laser rejection filter elements (also known as "pump" rejection elements) are of particular importance in the case of fully integrated analytical devices, such as the devices of the instant disclosure, since the integrated nature of these devices can place constraints on the aggregate thickness of all layers, and can also increase the angular bandwidth over which the rejection must be assured. For a non-integrated detector device, the deposited layers responsible for rejection of non-signal light can be many tens of microns thick (summing over several filters participating), but typically only need to reject light over an angular range of <10 degrees (including both field of view ("FOV") and filter tilt). For integrated devices such as the devices exemplified herein, however, the layers for pump rejection may need to be as thin as 5 microns or even less.

A further consideration with an integrated device is assuring that the rejected, non-signal light be terminated effectively (i.e., that it be efficiently removed from the optical system, for example by converting it to heat by absorption). For a non-integrated device, such termination is generally not critical, whereas for an integrated device, the reflected light can reach another detector site with a few (in principle, one) reflections, and furthermore, there is no local exit port for the rejected light to escape from the device. For these reasons, it is important to ensure that scattered light be converted to heat efficiently, ideally in one reflection. The detailed properties of two types of laser rejection filter elements suitable for use in the instant integrated devices is described in subsequent sections of the disclosure.

The color filtration elements and the laser rejection filter elements have features in common with one another, in that they are both designed to transmit certain wavelengths of light while blocking other wavelengths of light. The color filtration elements, however, serve to distinguish between wavelengths of light emitted from different emitters in the analyte, whereas the laser rejection filter elements are designed to block background noise arising from the waveguide or other excitation sources by scattering or other means. Accordingly, different color filtration elements are typically placed between the spatially-separated light from the lens element and the plurality of sensing regions in the detector layer, and a single laser rejection filter element—or multiple laser rejection filter elements with similar properties—is typically placed between the lens element and the detector layer, preferably between the color filtration layer and the detector layer. Suitable materials for use in the color filtration and laser rejection filter elements of the instant devices include, for example, amorphous silicon/silicon oxide interference stacks, polymer-like resists, doped PECVD oxides, organo-silicone with absorbing dyes, and the like. In preferred embodiments, the color filtration and laser rejection filter elements are thin-film interference filters. In more preferred embodiments, the color filtration and laser rejection filter elements are prepared from layers of amorphous silicon and silicon oxide. In other preferred embodiments, the laser rejection element is disposed between the color filtration layer and the detector layer.

Multilayer and Hybrid Laser Rejection Filter Elements

An ideal laser rejection filter provides for the deep rejection of optical energy at the wavelengths of sample excitation (e.g., OD>=6 at 532 nm for a typical laser illumination source), displays a broad window of high transmission at the wavelengths of sample emission, and further displays a small Stokes shift between the wavelengths of interest. In addition, it is desirable for a laser rejection filter to display minimal dispersion with angle and polarization, minimal thickness, and controlled termination. Furthermore, the filter stacks are preferably inexpensive and readily manufacturable under conditions (e.g., temperatures) suitable for the manufacture of other components of an integrated device.

In the case of dielectric thin-film laser rejection filters, it can sometimes be challenging in the design of such stacks to obtain adequate filter performance over a wide range of incident angles for the non-signal light. For example, given a specified wavelength range, an edge filter can provide high reflection efficiency but only within a particular range of incident angles (typically from normal incidence up to a certain value). In some of the integrated device designs described herein, in order to keep the scattering photons of the excitation source from reaching the detector, rejection over a wide angular spectrum may be desirable, especially to block photons with higher angle of incidence than a typical thin film stack can adequately support.

The instant disclosure addresses this problem by providing in one aspect multilayer laser rejection filters comprising a low index total internal reflection (TIR) layer in order to reduce transmission of high angle scattering light. Specifically, the low index layer is included in the device stack between the excitation source and the detector layer in order to minimize the background signal. Traditional dielectric long-pass filters, for example as shown in the left panel of FIG. 12A, reflect rays with lower angles of incidence (e.g., the middle rays in the drawing) more effectively than those with higher angle of incidence (e.g., the outer ray in the drawing). As shown in the right panel of FIG. 12A, when this filter design is incorporated into an integrated device, the high angle scattering light from the waveguide has a relatively higher chance of being transmitted through the filter stack and reaching the sensor. In the design solution of the instant disclosure, however, for example in the structure shown in the left panel of FIG. 12B, a low index TIR layer is added between the integrated excitation waveguide and a low angle rejection filter, such as a dielectric filter stack. The high angle scattering light experiences total internal reflection upon encountering the low index TIR layer, and after multiple bounces, exits the integrated device from the side. At the same time, the lower angle scattering light is transmitted through the low index TIR layer but is rejected by the dielectric filter stack. The combined effect of the TIR layer and the filter stack thus results in a barrier filter that blocks the scattering light with wide angular spectrum.

One candidate material for the low index TIR layer of the subject multilayer filter stack is air, with almost zero dispersion and low refractive index, but other low index materials are also suitable, including other gases, liquids, and solids having low refractive index and other suitable properties. The specific choice of material for the low index TIR layer will depend on the refractive index and other physical properties of the adjacent layers, as would be understood by those of ordinary skill in the art.

Figures 12A, 12B, 12C:
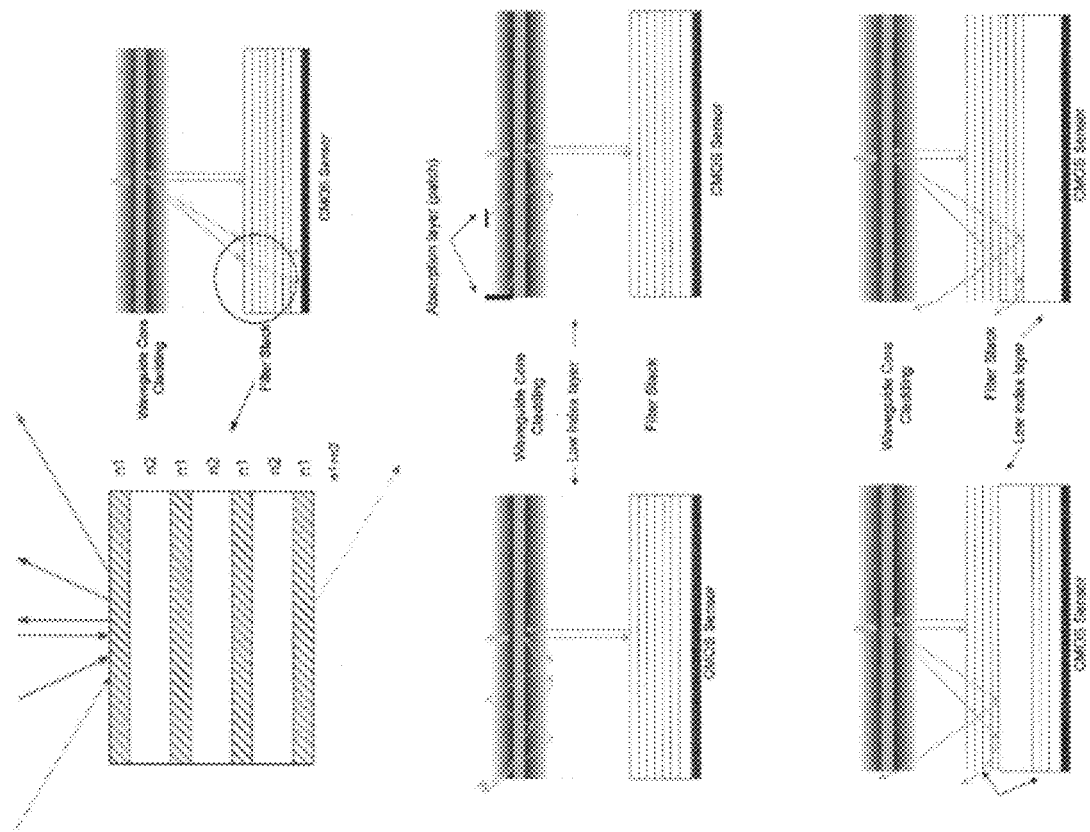
FIG. 12A illustrates the dependence on angle of incidence of optical rejection by a dielectric interference filter.
FIGS. 12B and 12C show schematically the inclusion of a low index layer at various places in an integrated device in order to increase the efficiency of optical rejection.

To help collect the scattered light and reduce the chance of multiple scattering, an absorption layer or patch can optionally be added to the device, as shown in the right panel of FIG. 12B. Materials for use in such an absorption layer are chosen based on their wavelength of absorption, their ability to dissipate optical energy, and their suitability in fabrication of the integrated device.

A variety of configurations of the above-described wide angular spectrum multilayer edge filter are possible, depending on the location, thickness, material choice, and number of layers of the low index layer(s). As described above, the low index layer can be placed directly below the excitation waveguide cladding, thus creating the shortest resonance cavity length and therefore limiting the chances for secondary scattering. The low index layer may, however, alternatively be placed within the thin film stack, as illustrated in the left panel of FIG. 12C, or between the thin film stack and the detection layer, as illustrated in the right panel of FIG. 12C. These configurations increase the resonance cavity length, and can therefore increase the chance of secondary scattering, but the configurations can advantageously facilitate manufacture of the device. Not shown in these examples is the lens element layer, which could be either above or below the laser rejection filter element, but which is preferably above the laser rejection filter.

In any case, incorporation of an additional TIR design constraint into the laser rejection filter design generates added value to the low index layer. For example, by incorporating the low index layer (or layers) as an integral component in the laser rejection filter design, e.g., because the filter is no longer limited to the thin film stack but can include the layers from the excitation waveguide to the detection layer, the integrated device performance can be fully optimized.

The instant disclosure further provides in another aspect laser rejection filter elements comprising a combination of dielectric stacks and absorption layers. Such hybrid filters take advantage of the complementary dependence on angle of incidence of interference coatings and absorption layers. Specifically, as mentioned above, interference coatings for rejection typically perform best for a cone centered on normal incidence, with dispersions that affect performance as a cosine of the angle in the interference thin films, whereas the performance of absorption rejection layers tends to increase with the angle of incidence, with dispersions that affect performance as a cosine of the angle in the absorbing layer. Owing to this complementary nature, a hybrid coating can be achieved with rejection of a target minimum over a wide angle range, in a minimum thickness. This thickness is reduced for higher refractive index thin films, and for lower refractive index absorbing layers. Note that thin films with absorption for the non-signal light (but minimal absorption of signal light) can be used effectively in a hybrid rejection filter.

As an example of an absorption dye suitable for use in combination with a dielectric filter stack, Aptina red1 has an absorption spectrum with high transmission above 600 nm. See Pang et al. (2011) *Lab Chip* 11:3698, FIG. 2. Although the thickness used in this publication was relatively large (8 µm), thinner layers can be used depending on the wavelength of laser excitation of the device. For example, a 5 µm layer provides OD>6 at 532 nm, a 4.7 µm layer provides OD>6 at 540 nm, and a 2.8 µm layer provides OD>6 at 562 nm. Other absorption dyes and pigments suitable for use in the instant hybrid filter stacks are readily identifiable by those of ordinary skill in the art.

Figure 13:
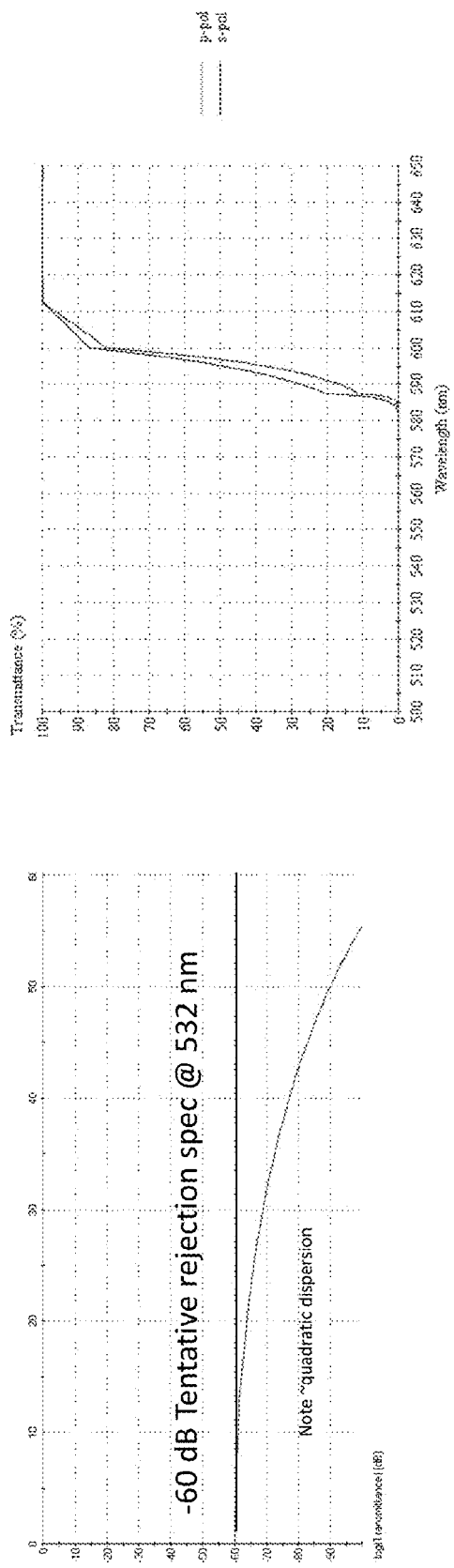
FIG. 13 illustrates the optical properties of an exemplary absorption dye layer.

In particular, laser rejection by an absorption dye layer, such as by a layer of Aptina red1 dye, advantageously displays no polarization dispersion, weak angle dispersion, and controlled termination of non-signal light. In addition, angularly non-uniform scatter can allow for further thinning of the absorption dye layer. If certain portions of the hemisphere have lower intensity non-signal light to be rejected, or if the intensity has known polarization dependence at some angles, this information can be used to further reduce the hybrid rejection filter thickness (for a given rejection target). The disadvantages of an absorption rejection filter, for example a layer of Aptina red1 dye, include a moderately large extinction coefficient, a relatively large thickness (5 μm), and the need to use sample dyes with a fairly large Stokes shift (532 nm to ~620 nm). These disadvantages can be offset to great extent, however, by the combination of an absorption layer with a dielectric stack in the instant hybrid rejection filters. FIG. 13 illustrates the weak angle dispersion (left panel) and lack of polarization dispersion (right panel) of an absorption dye layer.

Figure 14:
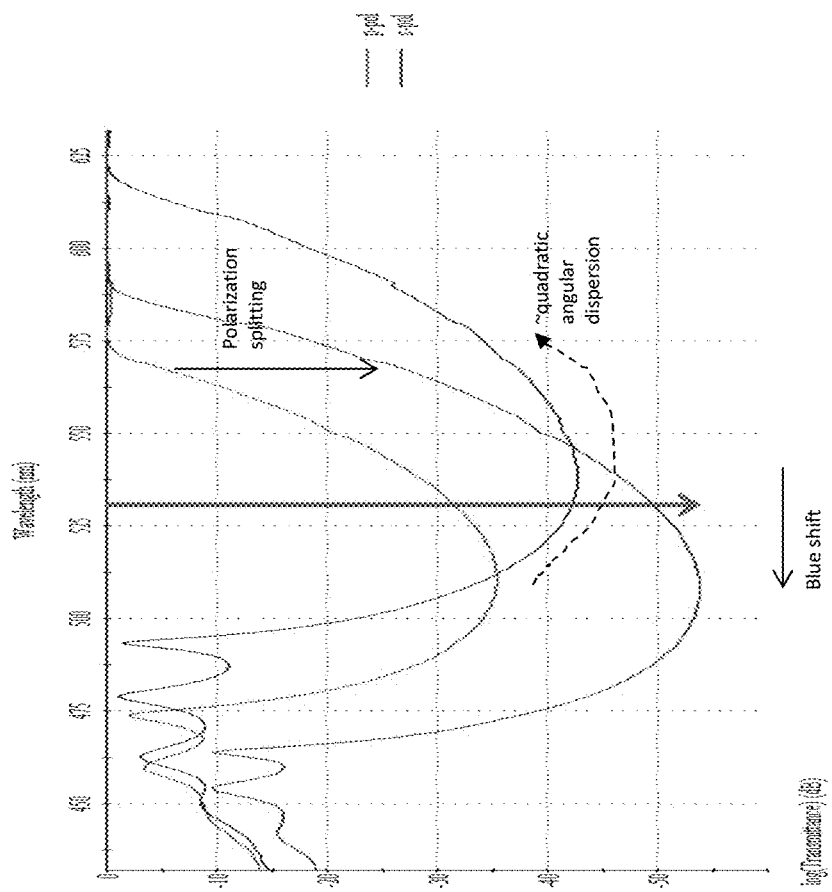
FIG. 14 illustrates the optical properties of an exemplary dielectric stack.

With respect to the dielectric stack component of a hybrid rejection filter, particularly advantageous rejection filters (especially those with low dependence on angle) are possible through the use of very high index materials for the interference portion of the filter. Exemplary materials finding utility for these purposes with 532 nm pumps are GaP (gallium phosphide) as the high index material, and $TiO_2$ as the low index material, although other suitable materials could be utilized, as described below, and as would be understood by those of ordinary skill in the art. Of note is that $TiO_2$ is typically used as a high index material for commonly produced coatings. FIG. 14 illustrates the advantageous properties of a $n_H/n_L$ GaP/$TiO_2$ dielectric stack, in particular the high extinction coefficient in the region of a 532 nm pump source (indicated by downward arrow), and a controllable Stokes shift. The material also displays, however, a significant angular dispersion (with a blue shift) between 0 and 45 degrees, and a significant polarization dispersion (splitting) between a p-polarized optical signal (upper trace near 570 nm) and an s-polarized optical signal (middle trace near 570 nm).

Figure 15A:
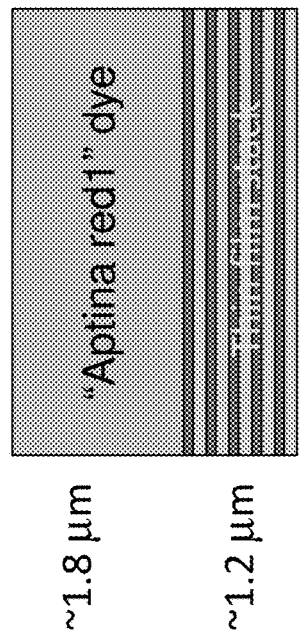
FIGS. 15A-15C schematically illustrate the structure of an exemplary hybrid laser rejection filter and the optical properties of the filter.
Figure 15B:
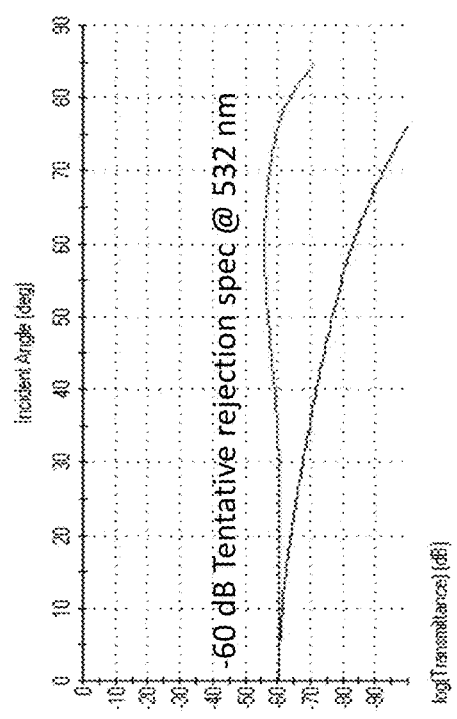
Figure 15C:
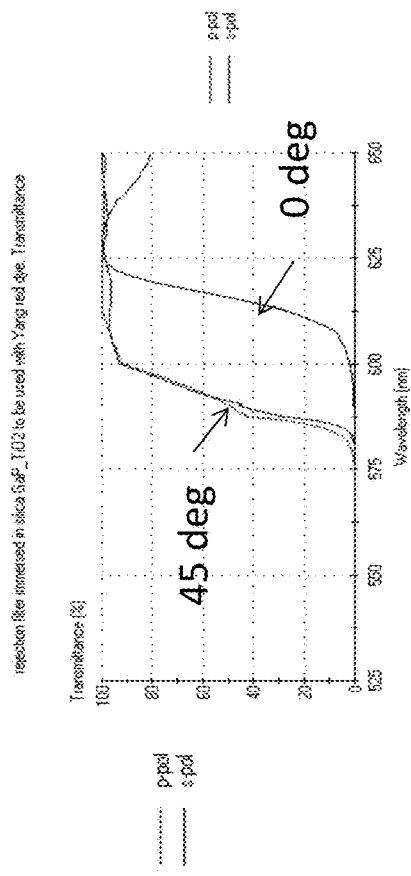

The advantages of combining an absorption dye layer and a dielectric interference stack in a single hybrid laser rejection filter are illustrated in FIGS. 15A-15C. Specifically, FIG. 15A shows an exemplary schematic design of such a hybrid filter, where the lower layer is a GaP/$TiO_2$ thin film stack and the upper layer is Aptina red1 dye. The hybrid filter achieves OD=6 rejection with a 3 μm total thickness, where OD=2 is provided by the absorption layer and OD=4 is provided by the interference layer. Polarization dispersion and angular dispersion can be compensated by the design of the filter element. As illustrated in FIGS. 15B and 15C, the effect of incident angle on transmittance is shown in FIG. 15B for p-polarized light (upper trace) and s-polarized light (lower trace), and the effect of wavelength on transmittance is shown in FIG. 15C for 45 degree incident light (left traces, p-polarized and s-polarized) and for 0 degree incident light (right trace). The absorption layer controls termination of transmitted light, and the overall design provides a tolerable Stokes shift, reasonable thickness, and good transmission at sample emission wavelengths.

Figure 16A:
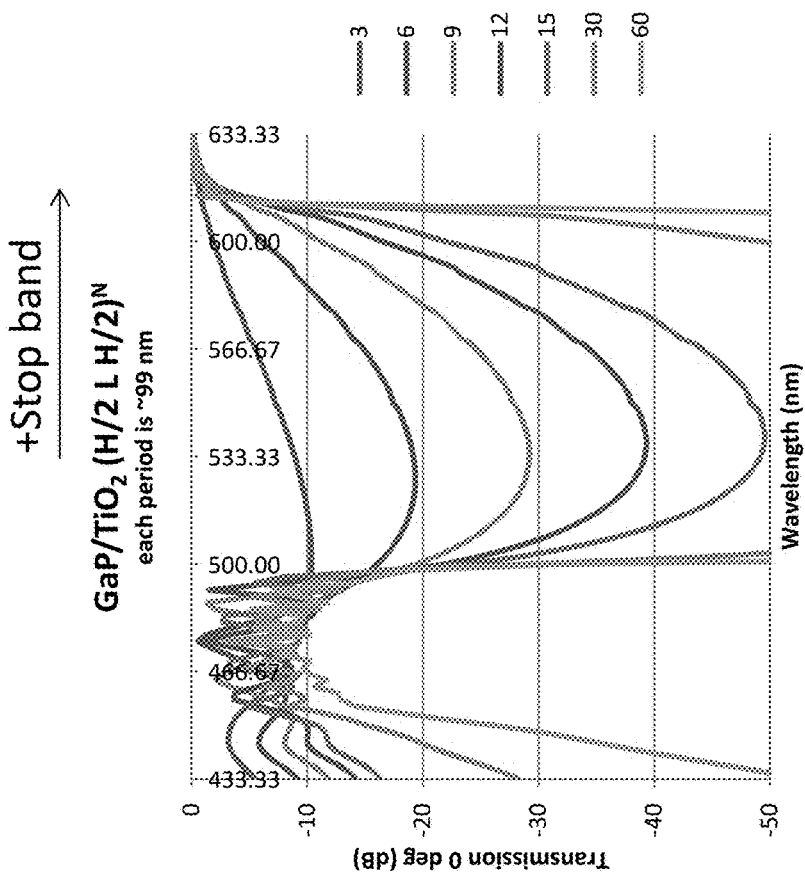

The optical properties of the dielectric stack component of the hybrid rejection filter can be modulated as desired by the choice of materials used to construct the stack, by the thickness of each layer, and by the number of layers. The dielectric materials utilized to fabricate interference filters are generally nonconductive materials, typically metal salts and metal oxides, having a specific refractive index. Exemplary materials include $SiO_2$, SiO, $Si_2O_3$, $Al_2O_3$, BeO, MgO, $CeF_3$, LiF, NaF, $MgF_2$, $CaF_2$, $TiO_2$, $Ta_2O_5$, $ZrO_2$, $HfO_2$, $Sb_2O_3$, $Y_2O_3$, $CeO_2$, $PbCl_2$, and ZnS. Also of use is GaP, due to its extremely high refractive index. The dielectric stack is preferably designed with overall structure $(H/2 \, H/2)^N$, where the H layer is a first material with relatively high refractive index and the L layer is a second material with relatively low refractive index. The physical thickness of each layer within the stack is chosen based on the desired optical properties, as is understood in the art. The value "N" is the number of repeating units of the structure within the parentheses and is an integer. Transmission in the stop band tends to zero (for a given incidence angle) with increasing overall thickness (e.g., as N increases). FIG. 16A illustrates the physical and optical properties of a GaP/$TiO_2$ stack with various values of N. FIG. 16B illustrates a further comparison of the physical and optical properties of interference stacks using different H and L pairs.

Figure 17B:
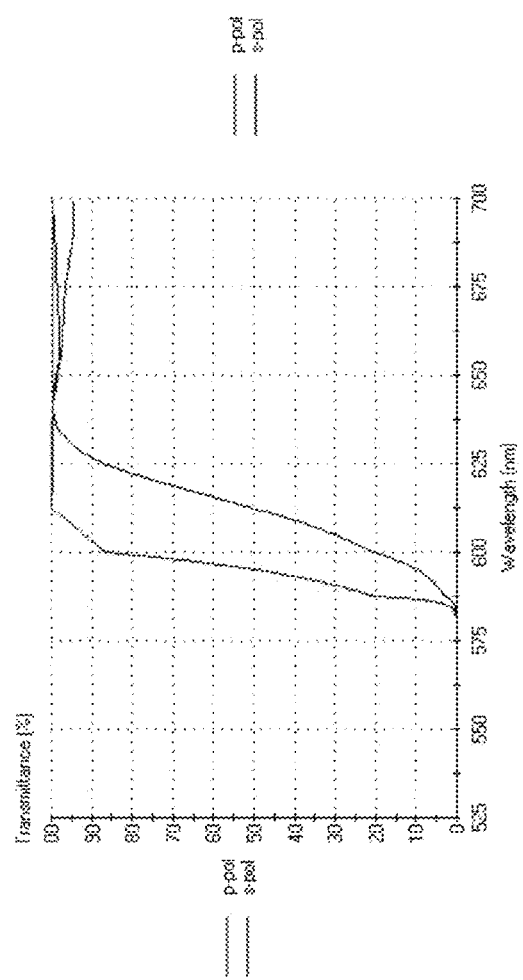
FIGS. 17A-17B illustrate the optical properties of a hybrid filter comprising a $TiO_2/Al_2O_3$ dielectric stack and an Aptina red1 absorption layer.
Figure 17A:
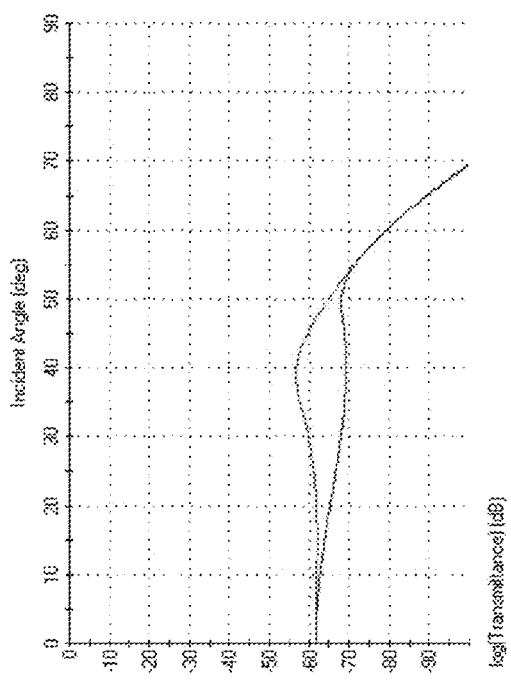
Figure 18B:
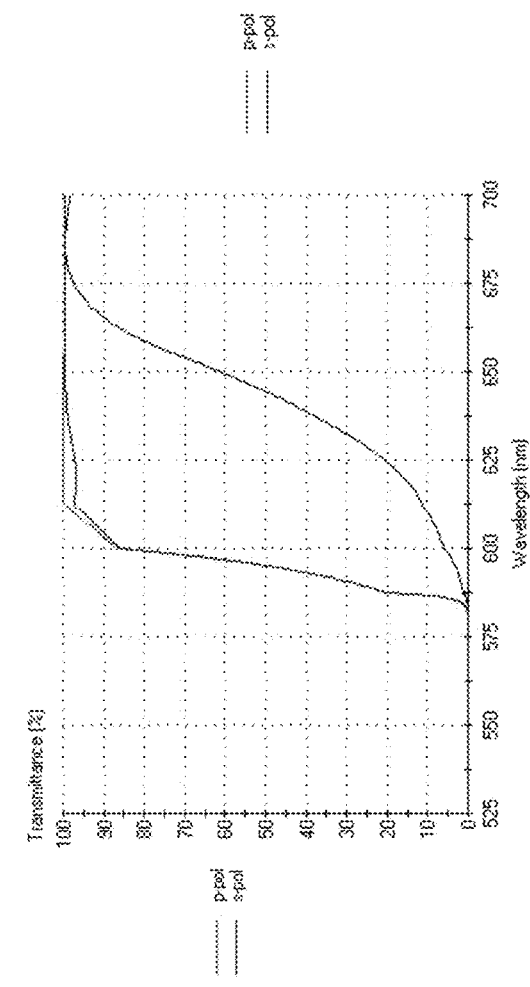
FIGS. 18A-18B illustrate the optical properties of a hybrid filter comprising a $TiO_2/SiO_2$ dielectric stack and an Aptina red1 absorption layer.
Figure 18A:
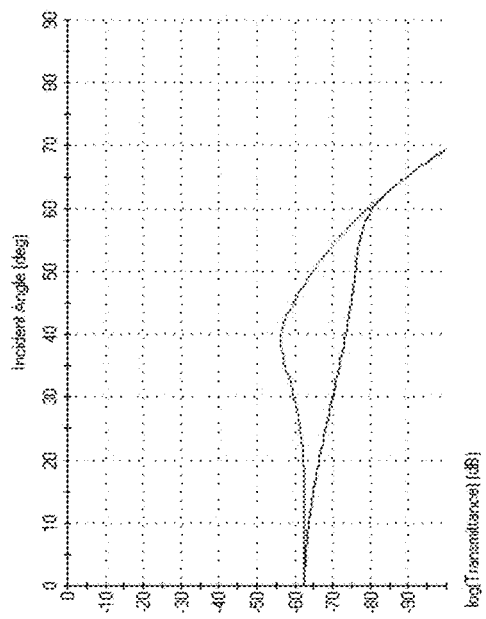

FIGS. 17A-17B and 18A-18B highlight the advantages of a GaP/$TiO_2$ stack in the hybrid rejection filter compared the use of other traditional dielectric stack materials. The optical properties of a hybrid rejection filter comprising a GaP/$TiO_2$ dielectric stack and an Aptina red1 absorption layer are described above and in FIGS. 15B and 15C. For comparison, the optical properties of a hybrid rejection filter comprising a $TiO_2/Al_2O_3$ dielectric stack and an Aptina red1 absorption layer are shown in FIGS. 17A and 17B, and the optical properties of a hybrid rejection filter comprising a $TiO_2/SiO_2$ dielectric stack and an Aptina red1 absorption layer are shown in FIGS. 18A and 18B. Importantly, the effective index of the $TiO_2/Al_2O_3$ and the $TiO_2/SiO_2$ stacks are lower than that of the GaP/$TiO_2$ stack, thus resulting in greater angle and polarization dispersion with these filters. Dispersion compensation for the $TiO_2/Al_2O_3$ hybrid rejection filter requires a 4.7 μm thickness (~3.6 μm for the absorption layer and ~1.1 μm for the dielectric stack). Dispersion compensation for the $TiO_2/SiO_2$ hybrid rejection filter requires a 4.5 μm thickness (~3.6 μm for the absorption layer and ~0.9 μm for the dielectric stack). As is apparent from FIG. 17B, the $TiO_2/Al_2O_3$ hybrid rejection filter would ideally be used with fluorescent dyes having relatively large Stokes shifts (e.g., 532 nm excitation and >635 nm emission), and the $TiO_2/SiO_2$ hybrid rejection filter would be best used with dyes having even larger Stokes shifts.

It should be understood that the order of the coatings can be varied in order to achieve optimal performance of the hybrid laser rejection filter elements. For example, the layers can be ordered with absorption first, interference coatings second, or vice versa. The absorbing material can be carried in a host material such as PMMA, and can be shaped or patterned to fit within limited volumes or to permit simpler integration.

The coatings can be created in different process steps, and joined into an assembly, as would be understood by those of ordinary skill in the art.

Accordingly, the instant disclosure thus provides in this aspect:

An array of integrated analytical devices, each device comprising:

a nanoscale emission volume;

a detector layer optically coupled to the nanoscale emission volume;

a diffractive beam shaping element disposed between the nanoscale emission volume and the detector layer;

a color filtration layer disposed between the diffractive beam shaping element and the detector layer;

an excitation source optically coupled to the nanoscale emission volume; and a laser rejection filter element disposed between the excitation source and the detector layer;

wherein light is emitted from the nanoscale emission volume by a plurality of emitters within the emission volume;

wherein the detector layer comprises a plurality of sensing regions; and wherein the diffractive beam shaping element spatially separates the light emitted from the nanoscale emission volume and directs the spatially-separated light through the color filtration layer to the plurality of sensing regions.

In some embodiments, the laser rejection filter element is a multilayer or a hybrid rejection filter element.

In specific embodiments, the laser rejection filter element is a multilayer filter element comprising a dielectric interference filter layer and a low index total internal reflectance layer. In more specific embodiments, each of the devices further comprises an absorption layer.

In other specific embodiments, the laser rejection filter element is a hybrid rejection filter element comprising an absorption layer and a dielectric stack layer.

In some embodiments, the laser rejection filter element displays low optical transmission at 532 nm and high optical transmission above 620 nm.

Dark Mirror Elements

In another aspect, the integrated analytical devices of the instant disclosure further comprise a dark mirror element. The term dark mirror is typically used to describe a surface with a coating that tends to absorb incident light without inherently scattering the light and one that also has low transmission. In integrated devices having a reservoir of non-sample fluorescent materials in the vicinity of the optical source, transmission of non-signal light into the reservoir of fluorescent materials can result in added noise background and should be avoided. Placing dark mirror coatings on areas of the device not directly active in passing signal (or illumination) light improve the overall ability of the integrated device to terminate non-signal light efficiently before the rejected non-signal light can impinge on another device site.

Figure 19A:
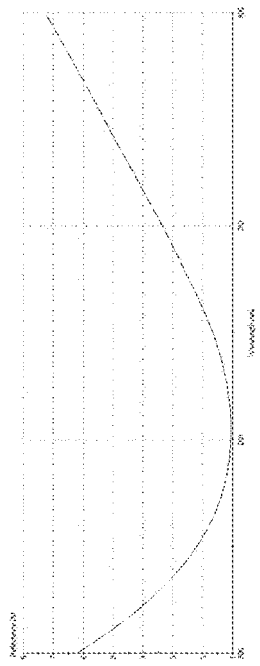
FIGS. 19A-19B illustrate the decreased reflectivity achieved by two exemplary dark mirror coatings.
Figure 19B:
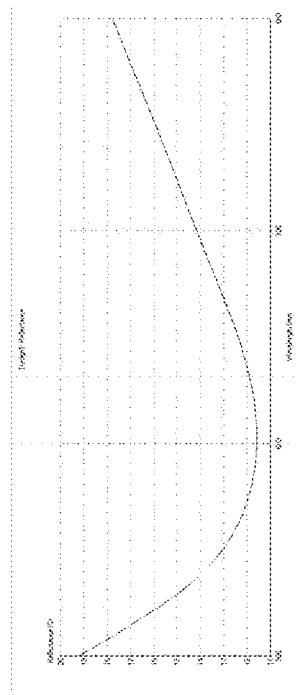

The optical properties of exemplary dark mirror coatings are illustrated in FIGS. 19A-19B, where FIG. 19A shows that a significant reduction in reflectivity can be achieved on a dielectric stack coated with Cr. With alternative coatings, for example a coating of TaN, even lower reflectivity is possible, as illustrated in FIG. 19B. Other materials are suitably used as dark mirror coatings, as would be understood by those of ordinary skill in the art.

Dark mirror coatings can be placed on scattering surfaces to decrease the probability of striking another device site within the signal angular bands, or to increase the path length for absorption before reaching another device site.

Dark mirror coatings that are angle-sensitive and/or polarization-sensitive can be used to permit highly efficient transmission of signal light, while achieving some target level of absorption of non-signal light.

Accordingly, the instant disclosure thus provides in this aspect:

An array of integrated analytical devices, each device comprising:
 a nanoscale emission volume;
 a detector layer optically coupled to the nanoscale emission volume;
 a diffractive beam shaping element disposed between the nanoscale emission volume and the detector layer;
 a color filtration layer disposed between the diffractive beam shaping element and the detector layer;
 a dark mirror filter element;
 wherein light is emitted from the nanoscale emission volume by a plurality of emitters within the emission volume;

wherein the detector layer comprises a plurality of sensing regions; and wherein the diffractive beam shaping element spatially separates the light emitted from the nanoscale emission volume and directs the spatially-separated light through the color filtration layer to the plurality of sensing regions.

In embodiments, the dark mirror element comprises a dark mirror coating on a scattering surface.

Arrays of Integrated Analytical Devices

In order to obtain the volumes of sequence information that can be desired for the widespread application of genetic sequencing, e.g., in research and diagnostics, high throughput systems are desired. As noted above, and by way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments.

As described above, and as shown in FIGS. 1A-1B, the template/DNA polymerase-primer complex of such a sequencing system is provided, typically immobilized, within an optically confined region, such as a zero mode waveguide (ZMW) or nanowell, or proximal to the surface of a transparent substrate, optical waveguide, or the like. Preferably, such reaction cells are arrayed in large numbers upon a substrate in order to achieve the scale necessary for genomic or other large-scale DNA sequencing approaches. Such arrays preferably comprise a complete integrated analytical device, such as, for example, the devices shown in the block diagrams of FIGS. 2 and 5. Examples of integrated systems comprising arrays of optical analytical devices are provided in U.S. Patent Application Publication Nos. 2012/0014837; 2012/0019828; and 2012/0021525.

Arrays of integrated analytical devices, such as arrays of devices comprising ZMWs/nanowells, can be fabricated at ultra-high density, providing anywhere from 1000 ZMWs per $cm^2$, to 1,000,000 ZMWs per $cm^2$, or more. Thus, at any given time, it can be possible to analyze the reactions occurring in from 100, 1000, 3000, 5000, 10,000, 20,000, 50,000, 100,000, 1 Million, 10 Million, or even more nanoscale emission volumes or other reaction regions within a single analytical system or even on a single substrate.

Using the foregoing systems, simultaneous targeted illumination of thousands or tens of thousands of ZMWs/nanowells in an array has been described. However, as the desire for multiplex increases, the density of ZMWs on an array, and the ability to provide targeted illumination of such arrays, increases in difficulty, as issues of ZMW cross-talk (signals from neighboring ZMWs contaminating each other as they exit the array), decreased signal:noise ratios arising from higher levels of denser illumination, and the like, increase. The arrays and methods of the instant invention address some of these issues.

The position on the detector upon which a given signal is incident is indicative of (1) the originating emission volume within a ZMW/nanowell in the array, and (2) the emission characteristics of the signal component, which is used, for example, to identify the type of fluorescently labeled nucleotide analog incorporated in an extension reaction. As noted above, the detector can include in some cases a plurality of sensing regions, each for detecting light passed from the emission volume through a diffractive beam shaping element and a color filtration layer to a detector layer. For example, in the case of sequencing, the sensor for each reaction cell can have 4 elements, one for each of the four bases. In some cases, the sensing regions can provide color discrimination, although the color filtration layer is preferably used to distinguish the appropriate color of light for the appropriate sensing region. In these embodiments, the sensing regions detect intensity of signal only, without discriminating color. In some cases, the sensor elements identify the incorporated nucleotide using a combination of emission characteristics.

FIGS. 20A-20D illustrate exemplary device layouts usefully employed in the arrays of the instant disclosure. In each case, the arrays are viewed from above, with dark circles representing the ZMWs/nanowells. As shown, the ZMWs/nanowells are positioned directly above waveguides, which are identified as broad arrows. In the case of the arrays shown in FIGS. 20A and 20C, the "pitch" of the waveguide is 2 columns (i.e., the waveguides are separated by the width of two columns of sensing regions/pixels), whereas for the arrays of FIGS. 20B and 20D, the pitch of the waveguide is 1 column (i.e., the waveguides are separated by the width of one column of sensing regions/pixels). The spatial separation of emitted light effected by the diffractive beam shaping elements in each of the arrays is indicated by the two thin arrows associated with some of the ZMW/nanowells. For example, in the devices of FIG. 20A, the diffractive beam shaping elements direct emitted light onto the two sensing regions that are aligned perpendicularly (i.e., at 90°) to the waveguide. In the devices of FIG. 20B, the diffractive beam shaping elements direct emitted light onto the two sensing regions that are collinear (i.e., at 0°) with the waveguide. For the devices of FIGS. 20C and 20D, the diffractive beam shaping elements direct emitted light onto the two sensing regions that are diagonal (i.e., at 45°) relative to the waveguide. As is apparent from the drawings, the devices of FIGS. 20C and 20D differ with respect to the pitch of the respective waveguides.

Figure 21:
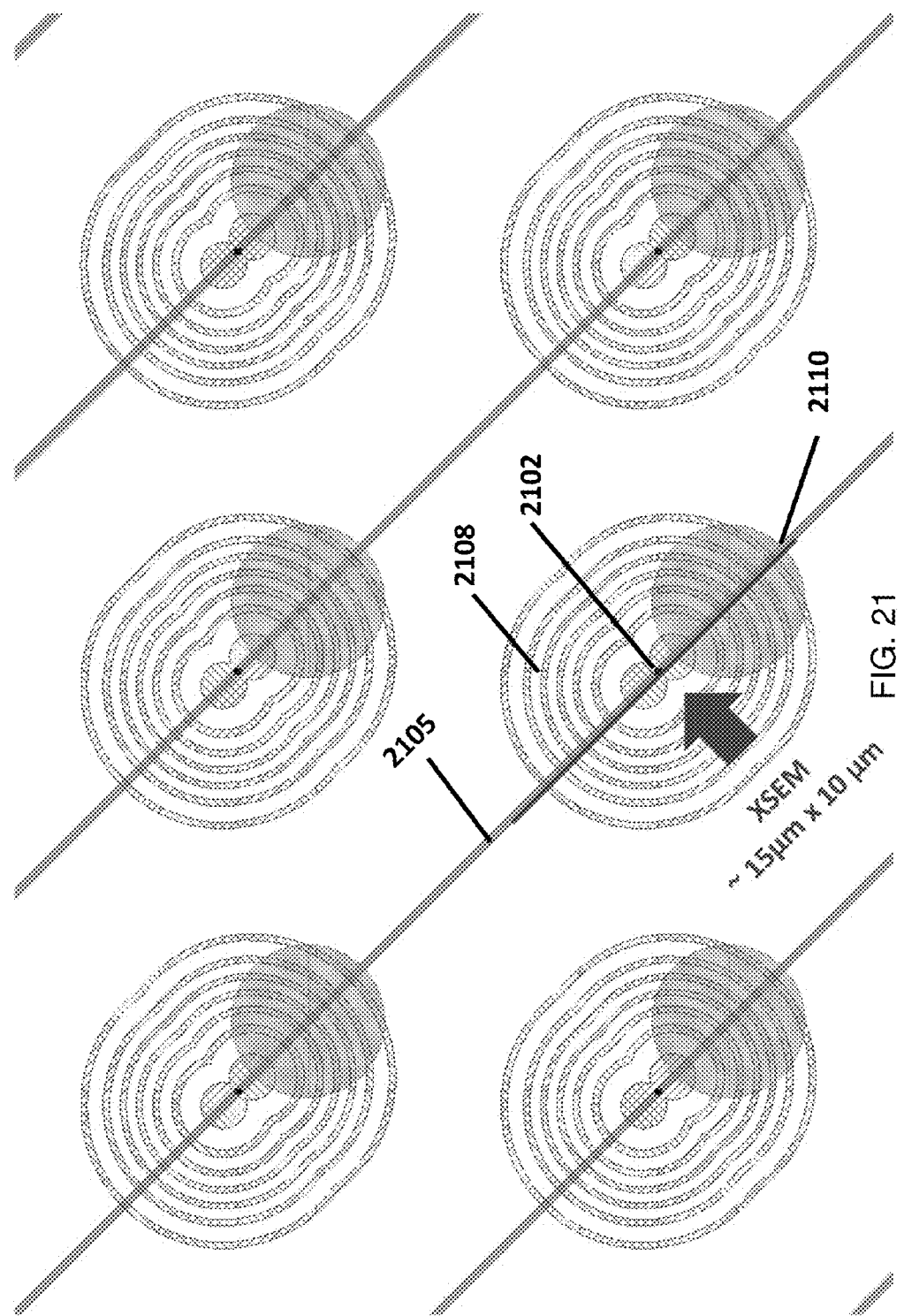
FIG. 21 illustrates specific features of an integrated analytical device within an array of exemplary devices of the invention.

FIG. 21 illustrates an array of devices, as viewed from above, wherein the design of an exemplary diffractive beam shaping element 2108 within a specific unit cell is shown in more detail. Also labeled within the unit cell is a ZMW/nanowell 2102, a waveguide 2105, and one of the two color filtration regions 2110 that would be positioned over a sensing region of the detection layer. In these devices, the sensing regions would be collinear with the waveguide, and the waveguide pitch would be 1 column. Not shown in this drawing is the second color filtration region and various other features of the devices that have been described above, e.g., aperture elements, laser rejection elements, metallic and anti-reflective surface layers, waveguide cladding layers, electronic circuitry, and so forth.

Figure 22A:
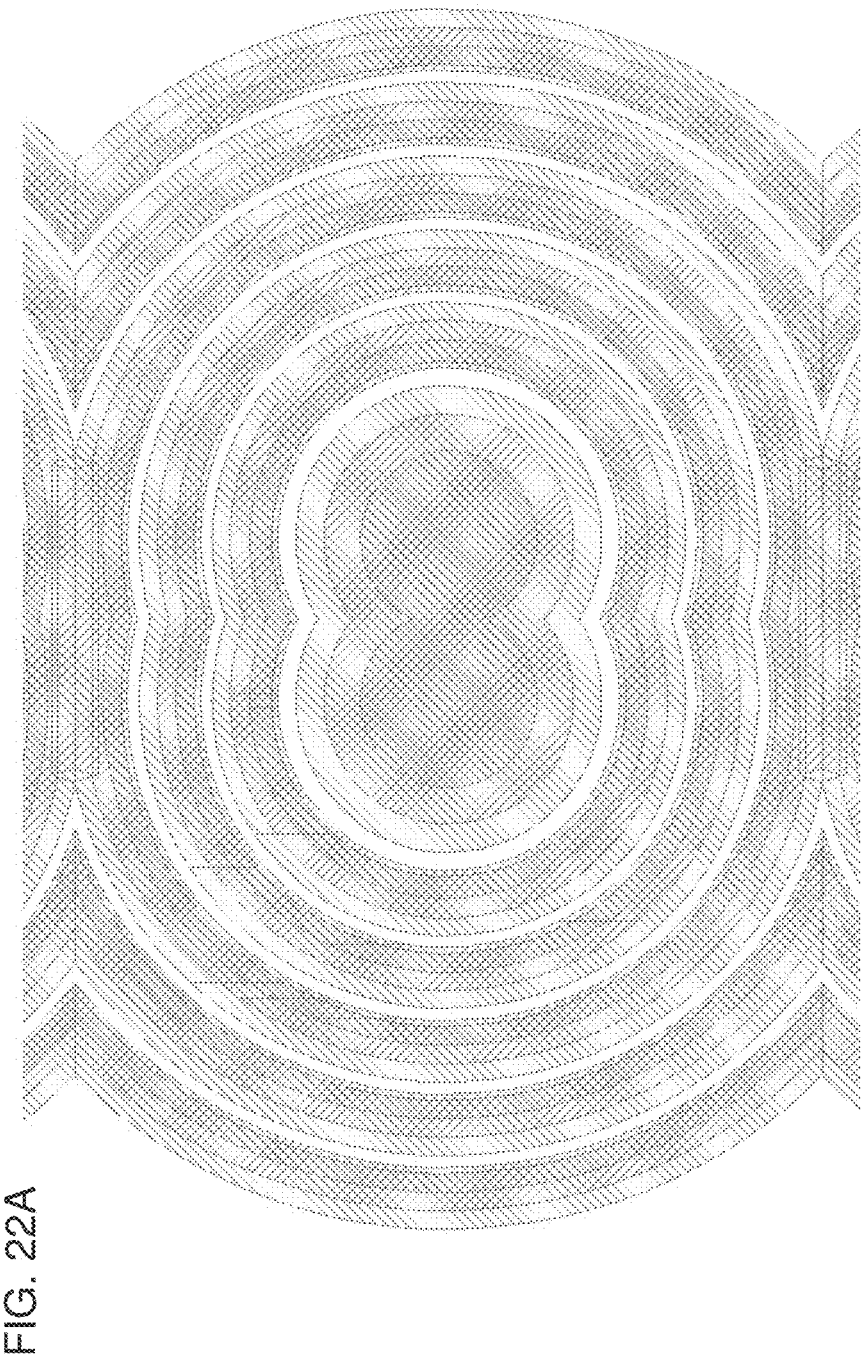
FIGS. 22A-22E illustrate components of an exemplary unit cell of the instant devices and their general features.
Figure 22C:
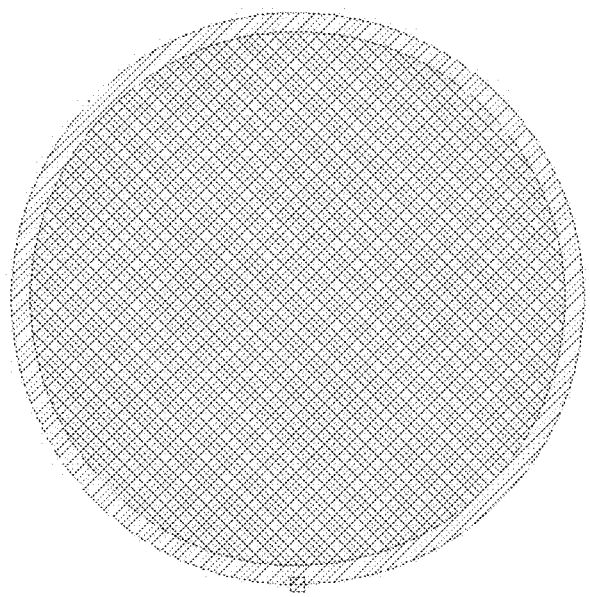
Figure 22B:
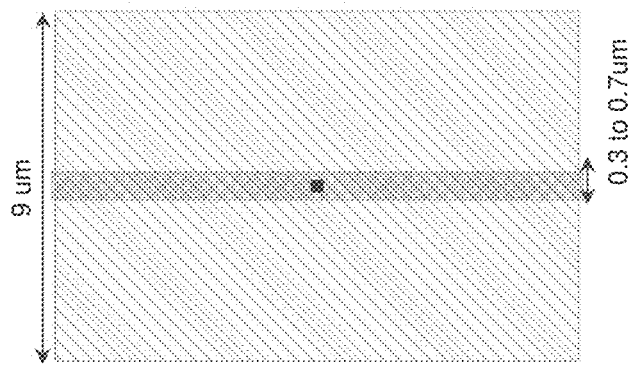
Figure 22E:
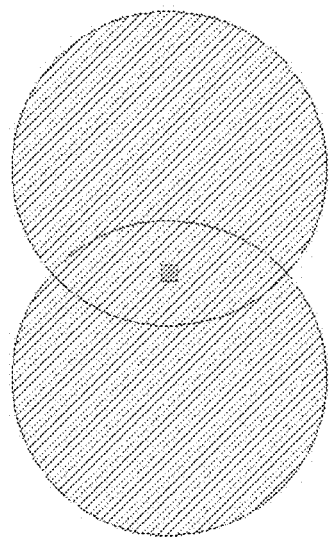
Figure 22D:
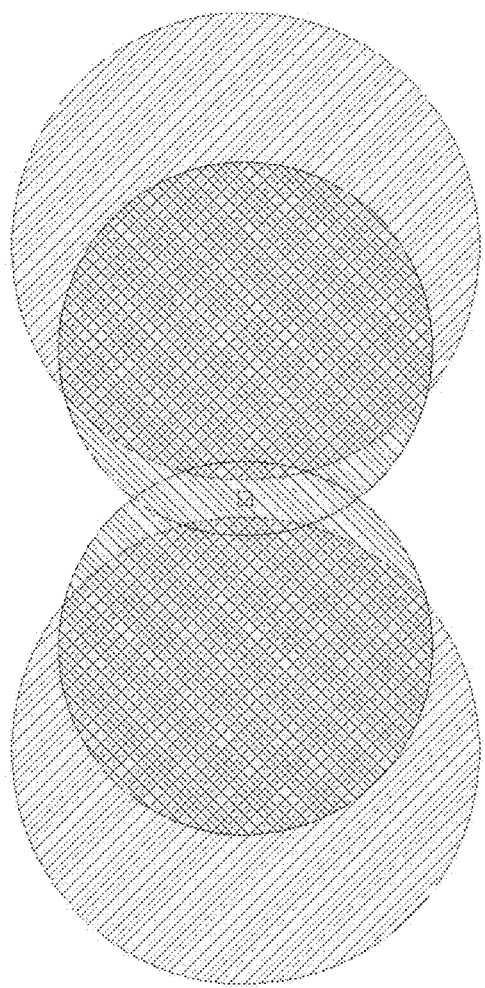

FIGS. 22A-22E show the various typical elements used to build an exemplary unit cell of the instant devices and their general features. The elements are viewed from above the plane of the unit cell. Specifically, FIG. 22A illustrates a diffractive beam shaping element, where the dimensions of the diffractive beam shaping element (and also the unit cell itself) are roughly 10 μm×15 μm. FIG. 22B illustrates a ZMW/nanowell (shown as a small square) and its associated waveguide. As indicated, the width of the waveguide is roughly 0.3 to 0.7 μm, and it is fabricated in a trench of approximately 9 μm wide. FIG. 22C illustrates two circular color filtration regions of radius 2.8 μm and 3.0 μm. As assembled within the device, however, each of the color filtration regions would be offset approximately 3.0 μm relative to the ZMW/nanowell. FIG. 22D illustrates a ZMW/nanowell (shown as a small square) and two associated aperture elements, which correspond in each case to two offset transparent circles. The larger aperture element layer, with circles having diameters of approximately 2.5 μm, and offset approximately +/−2.7 μm relative to the ZMW/nanowell, would typically be disposed between the detector layer and the laser rejection layer/color filtration layer. The smaller aperture element layer, with circles having diameters of approximately 2.0 μm, and offset approximately +/−1.6 μm relative to the ZMW/nanowell, would typically be disposed between the color filtration layer and the diffractive beam shaping element layer. FIG. 22E illustrates a ZMW/nanowell (shown as a small square) and a third associated aperture element, corresponding to two offset transparent circles. These circles have diameters of approximately 1.5 μm, and are offset approximately +/−1.0 μm relative to the ZMW/nanowell. This aperture element would typically be disposed between the diffractive beam shaping element layer and the waveguide.

Figure 23:
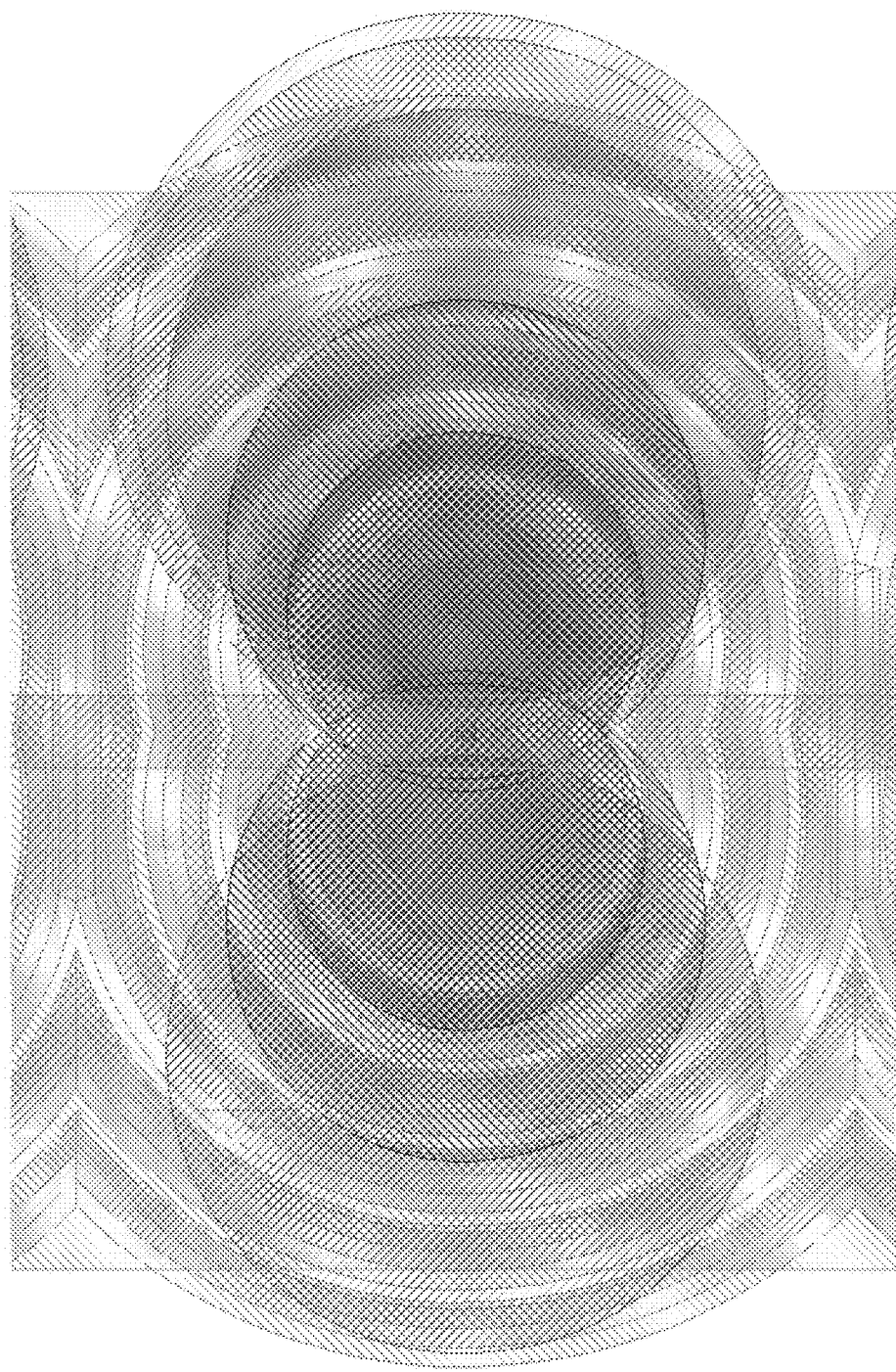
FIG. 23 illustrates an assembled view of the components of FIGS. 22A-22E.

FIG. 23 illustrates a schematic representation of the assembly of the components of FIGS. 22A-22E into an exemplary integrated unit cell device of the invention. The ZMW/nanowell is apparent as a small square in the center of the unit cell, and the waveguide is shown as the vertical parallel lines straddling the ZMW/nanowell. The exemplary device includes from top to bottom, in the following order, the ZMW/nanowell, the waveguide, a third aperture element, a diffractive beam shaping element, a second aperture element, a color filtration layer, a first aperture element, and a detector layer. The exemplary device can optionally include a laser rejection layer between the color filtration layer and the first aperture element, or at another location in the device. The diffractive beam shaping element in this embodiment of the nanoscale integrated analytical device would direct light emitted from the ZMW/nanowell perpendicular to the waveguide. In other words, this exemplary device would correspond to the array layout shown in FIG. 20A.

Figure 24:
FIG. 24 provides a cross-sectional view of an exemplary unit cell of the instant disclosure.
Figure 25:
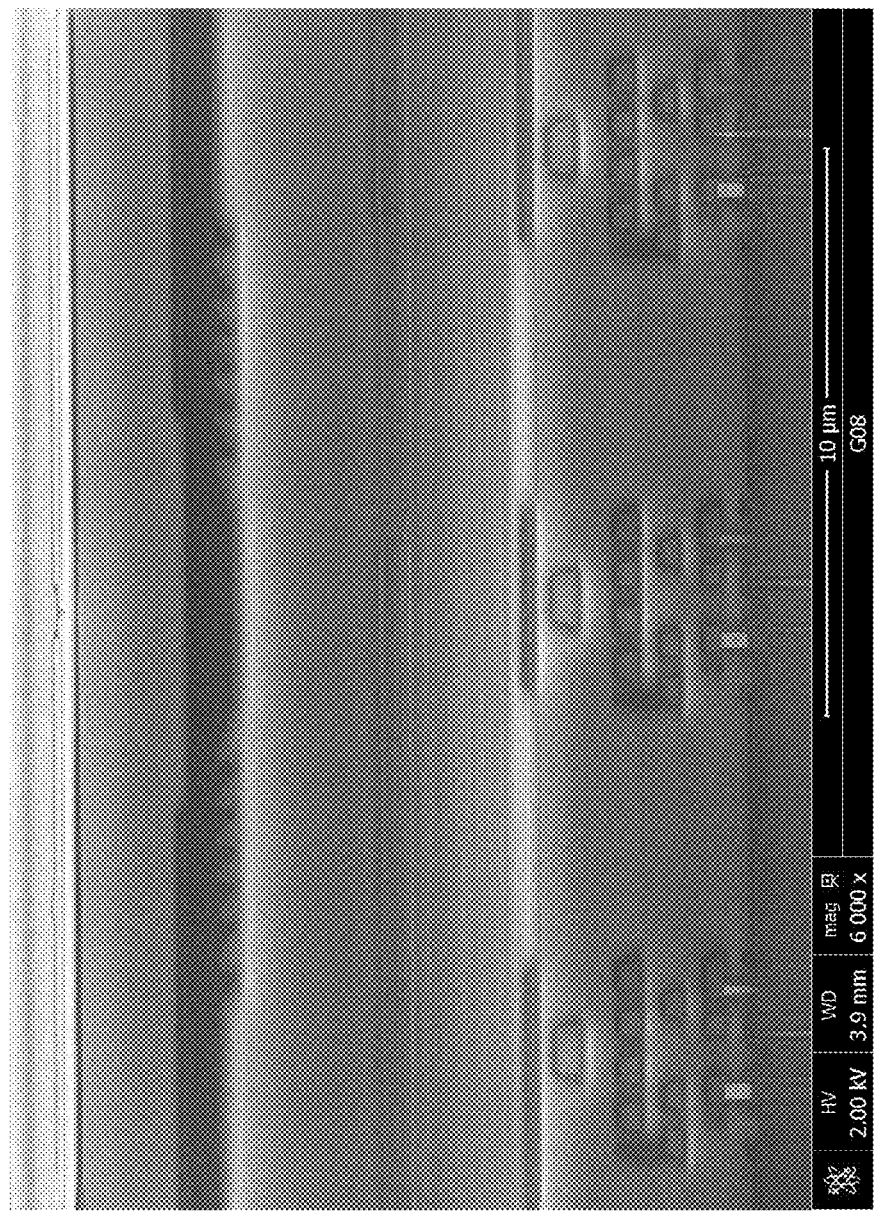
FIG. 25 illustrates a cross-sectional SEM micrograph of an exemplary integrated device fabricated according to the instant disclosure.

FIG. 24 provides a more detailed schematic cross-section of the device described in FIG. 23, including dimensions and exemplary materials. A cross-sectional SEM micrograph of a device fabricated according to the design of FIG. 24 is shown in FIG. 25.

Methods for Producing Arrays of Integrated Analytical Devices

In another aspect, the instant disclosure provides methods for producing arrays of integrated analytical devices. As described above, such arrays are useful, for example, in the large-scale sequencing of nucleic acids, including in particular, genomic sequencing. Such arrays can be produced by a variety of methods. One preferred approach for producing the instant arrays involves the use of microfabrication methods such as semiconductor or MEMS processing methods, which have been highly developed for the production of integrated circuits. Similar processes have been used to create MEMS (micro electromechanical systems) for a variety of applications including inkjet printers, accelerometers, pressure transducers, and displays (such as digital micromirror displays (DMDs)). Microfabrication methods can be applied to a large substrate such as a wafer, which can later be diced into many devices, allowing for the production of many devices at one time.

The methods of the invention may, for example, apply resist processes, such as photoresists, to define structural elements on substrates or other layers. Etching processes can be used to produce three-dimensional structures, including component structures in the integrated analytical device. Deposition processes can be used to add layers onto the devices. Other semiconductor processes such as ashing, polishing, release, liftoff, and wet cleans can also be employed to create the structures of the invention, as described in more detail below.

For example, lithographic techniques can be used to define a mask layer out of polymeric materials, such as photoresists, using e.g., conventional photolithography, e-beam lithography, or the like. Alternatively, lithographic techniques can be applied in conjunction with layer deposition methods to deposit metal mask layers, e.g., using aluminum, gold, platinum, chrome, or other conventionally used metals, or other inorganic mask layers, e.g., silica based substrates such as silicon, $SiO_2$, or the like. Alternatively, negative tone processes can be employed to define pillars of resists that correspond to, for example, nanowells. See, e.g., U.S. Pat. No. 7,170,050, which is incorporated by reference herein in its entirety for all purposes. The mask layer can then be deposited over the resist pillars and the pillars are subsequently removed. In particularly preferred aspects, both the underlying substrate and the mask layer are fabricated from the same material, which in particularly preferred aspects, is a transparent substrate material such as an $SiO_2$-based substrate such as glass, quartz, or fused silica. By providing the mask and underlying layers of the same material, one can ensure that the two layers have the same interactivity with the environments to which they are exposed, and thus minimize any hybrid surface interactions.

In the case of $SiO_2$-based substrates and mask layers, conventional fabrication processes can be employed. For example, a glass substrate bearing a surface-exposed feature, such as a waveguide, can have a layer of resist deposited over its surface. A negative of the mask layer is then defined by appropriate exposure and development of the resist layer to provide resist islands where one wishes to retain access to the underlying feature. The mask layer is then deposited over the surface and the remaining resist islands are removed, e.g., through a lift off process, to provide the openings to the underlying feature. In the case of metal layers, deposition can be accomplished through a number of means, including evaporation, sputtering or the like. Such processes are described in, e.g., U.S. Pat. No. 7,170,050. In the case of silica based mask layers, a chemical vapor deposition (CVD) process can be employed to deposit a silicon layer onto the surface. Following lift off of the resist layer, a thermal oxidation process can convert the mask layer to $SiO_2$. Alternatively, etching methods can be used to etch access points to underlying layers using conventional processes. For example, a silicon layer can be deposited over an underlying substrate. A resist layer is then deposited over the surface of the silicon layer and exposed and developed to define the pattern of the mask. The access points are then etched from the silicon layer using an appropriate differential etch to remove silicon but not the underlying $SiO_2$ substrate. Once the mask layer is defined, the silicon layer is again converted to $SiO_2$ using, e.g., a thermal oxidation process.

One aspect of the invention relates to a process for producing arrays of integrated analytical devices comprising the steps of: providing a substrate layer, which can be a light-sensitive detector layer, such as a CMOS sensor layer, a CCD layer, or the like; depositing a laser rejection filter element layer on the substrate layer; depositing a color filtration layer on the laser rejection filter element layer; depositing a lens element layer, specifically a layer including a diffractive beam shaping element, on the color filtration layer; depositing an excitation waveguide layer on the lens element layer, depositing a ZMW layer on the lens element layer; and patterning and etching the ZMW material to define an array of nanowells penetrating into the upper cladding of the ZMW layer. Unless specifically described, the order of the steps of the processes described herein can be altered, where suitable. In some embodiments, additional steps can be added, in particular the deposition and patterning of one or more aperture layers between the other layers of the device. A specific example of such a fabrication process is provided in detail below. Further examples of processes useful in the production of arrays of integrated analytical devices can be found in U.S. patent application Ser. No. 13/920,037, which is incorporated by reference herein in its entirety for all purposes.

In each of the above exemplary microfabrication techniques, the process begins with a clean substrate layer. The substrate layer used in the instant methods can be of any suitable rigid material. The substrate layer material can comprise, for example, an inorganic oxide material such as silica. A preferred substrate layer material comprises a detector layer, such as, for example, a CMOS wafer, i.e., a wafer made up of CMOS sensors or CCD arrays. See, for example, *CMOS Imagers From Phototransduction to Image Processing* (2004) Yadid-Pecht and Etienne-Cummings, eds.; Springer; *CMOS/CCD Sensors and Camera Systems* (2007) Holst and Lomheim; SPIE Press.

As mentioned above, the methods of the invention in some cases use resists for defining and producing structures with lithography. These resists can be, for example, photoresists or e-beam resists. The photoresists can be developed using UV, deep UV, G-line, H-line, I-line or other suitable wavelength or set of wavelengths. The type of resist that is used, and therefore the type of instrumentation that is employed for processing, will depend on the dimensions of the features that are created. In many processes described herein, higher resolution resists and equipment will be used for the production of the nanowell which corresponds to the reaction volume, where the size of the nanowell can be on the order of 10 nm to 500 nm, and a lower resolution resist and associated instrumentation is used for the creation of the rest of the integrated analytical device, which can have features on the dimensions of 1 micron to 20 microns. Many resists are known in the art, and many are available commercially from companies such as Rohm and Haas and Shipley. The resists used in the processes of the invention can be negative or positive photoresists. Where a process is described herein using a negative photoresist, it is to be understood that a suitable positive photoresist can also be employed where practical, and vice versa. Where appropriate, chemical amplification can also be employed in order to increase the sensitivity of the resist. The removal of the resist, the cleaning, rinsing, ashing, and drying of the substrate can be performed as appropriate and as taught and known in the art.

In some cases, the tools used for photolithography of the nanowell use photolithography exposure tool capable of creating structures having feature sizes of about of 10 nm to about 100 nm. Such systems include, for example, an AMSL XT1250 exposure tool.

Etching processes are used in some aspects of the invention in order to produce the three dimensional features in a substrate or in other layers, to fashion, for example, optical elements or lenses, or reaction volumes such as nanowells. The etching process that is used will depend on the type of material used, the dimensions of the features, and the resist system. In some cases wet etching or wet chemical etching is employed. Electrochemical etching can also be employed. In some embodiments plasma etching or reactive ion etching (RIE) is used as an etching process. Deep reactive ion etching (DRIE) can also be employed, for example, where structures having high aspect ratio are desired. Dry vapor phase etching, for example with xenon difluoride, can also be used. Bulk micromachining or surface micromachining can be used as appropriate to create the device structures of the disclosure. The etching used in the methods of the disclosure can be gray-scale etching. The conditions of the resist formation and etching are controlled to produce side walls having the desired geometries, such as having the desired side-wall angle.

Some processes of the invention involve the deposition of reflective layers, or cladding layers. The deposition of these reflective layers can be accomplished by wet processes including spinning on layers from solution, or by gas-phase processes. Suitable processes include electroplating, sputter deposition, physical vapor deposition, evaporation, molecular beam epitaxy, atomic layer deposition, and chemical vapor deposition. Metals can be used as the reflective layer and the cladding layer. Suitable metals include gold, nickel, aluminum, chromium, titanium, platinum, and silver. The reflective and/or cladding layers can comprise aluminum, which can be deposited by sputtering, for example using a commercially available sputter tool available from CVC, Novellus, or MRC.

Where layers are deposited during the processes of the invention, in some cases, the layers are treated before moving on to the next step in the process. For example, the deposited layer can be annealed, planarized, cleaned, passivated, or lightly etched in order to improve its properties.

In some methods of the invention, protective layers or sacrificial layers are deposited. The protective layers can be polymeric layers, or can be inorganic layers. Suitable protective or sacrificial layers include germanium (Ge) and amorphous silicon (a-Si). Protective layers can be used to produce features as described herein. The type of material for the protective or sacrificial layer can be chosen for its selective reactivity, for example to wet chemical etchants. For example, in some cases, the ability to selectively etch germanium with heated hydrogen peroxide in the presence of silicon dioxide and aluminum results in its being utilized to produce optical structures combined with nanowells.

In some processes, a pull-back process can be employed. A pull-back process generally involves etching in from the edges of a feature within a layer in order to reduce the dimensions of the feature. Pull-back can be performed using a wet chemical reagent that selectively reacts with a layer which has exposed edges. In some cases a germanium layer is pulled back using hydrogen peroxide.

Some methods employ a polishing step to remove a surface region from a surface. Suitable methods include chemical-mechanical polishing or chemical-mechanical planarization (CMP).

Some methods of the invention incorporate a planarization layer. The method for depositing the planarization layer depends on the type of material that is used. The planarization layer can be a hard material, such as an inorganic material, for example silicon nitride; it can be a metallic material such as aluminum; or it can be a soft material, such as a polymeric material, e.g. an organic or silicon based polymer. The planarization layer can be a glass, such as a silicon dioxide material. In some cases, the planarization layer comprises a spin-on glass such as a silicate, phosphosilicate or siloxane material. Suitable spin-on glass materials are available, for example, from Honeywell Corporation. The planarization layer can comprise, for example, a glass doped with other agents to control its melting properties, such a boro-phosphoro-silicate glass (BPSG). Suitable polymeric planarization materials include, for example, polyimides.

After the arrays of the instant disclosure are complete, such as by, for example, following the process flow of the example below, the arrays can be further processed, such as, for example, by separating the arrays into individual chips and readying them for sequencing. The further processing steps will depend on the situation but can typically include the following treatments: surface treatment (a series of wet/vapor phase treatments to put down a specific surface that attracts the DNA polymerase enzyme to the bottom of the nanowell); stacking (a process to protect the top surface of the surface-treated device wafer and, in some cases, creating a well for the sequencing mixture); thinning (a process in which the composite top-plated and surface-treated device wafer can be thinned—including grinding lapping, polishing, or other treatments); dicing (a process in which the composite wafer is divided into individual chips using a standard semiconductor dicing saw); and packaging (a process involving a standard pick and place tool to mount the chips onto a substrate and create electrical/optical outputs for data collection). These further processing steps are either known in the art or are disclosed in references such as U.S. Patent Application Publication Nos. 2008/0176769 and 2011/0183409, which are incorporated by reference herein in their entireties for all purposes.

As just noted, the arrays of the invention can be incorporated into analysis systems for analyzing the multiple reactions occurring in the nanowells of the array. The arrays described herein typically have nanowells that are accessible to fluid from the top, and that are accessible for optical analysis from the bottom. The arrays are thus generally incorporated into a vessel into which a reaction mixture of interest is introduced. In some cases, the individual nanowells are all in contact with one volume of fluid, which can have, for example, multiple nucleic acid template molecules which can be analyzed, and which can have the nucleotides, cofactors, and other additives for carrying out the reaction to be analyzed.

The vessel that comprises the array can be placed within an instrument which has the appropriate optical components, computer controls, and data analysis systems. The vessel comprising the array can be held within the instrument such that the reaction conditions, such as the vessel temperature and vessel atmospheric conditions, can be controlled. The vessel atmospheric conditions can comprise the makeup of the gas above the sample, for example the humidity, and the level of other gaseous species such as oxygen.

It will be readily apparent to one of ordinary skill in the relevant arts that other suitable modifications and adaptations to the methods and applications described herein can be made without departing from the scope of the invention or any embodiment thereof. Having now described the present invention in detail, the same will be more clearly understood by reference to the following Example, which is included herewith for purposes of illustration only and is not intended to be limiting of the invention.

EXAMPLE

Figures 26C, 26D:
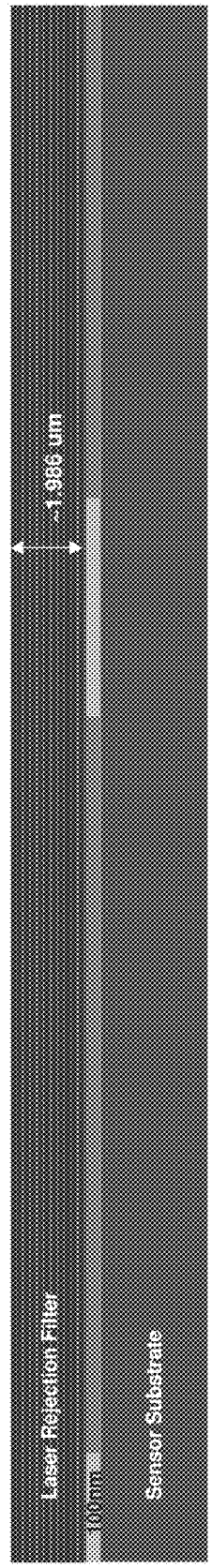
FIGS. 26A-26R show an exemplary process flow for the fabrication of an array of integrated analytical devices comprising a diffractive beam shaping element.
Figure 26J:
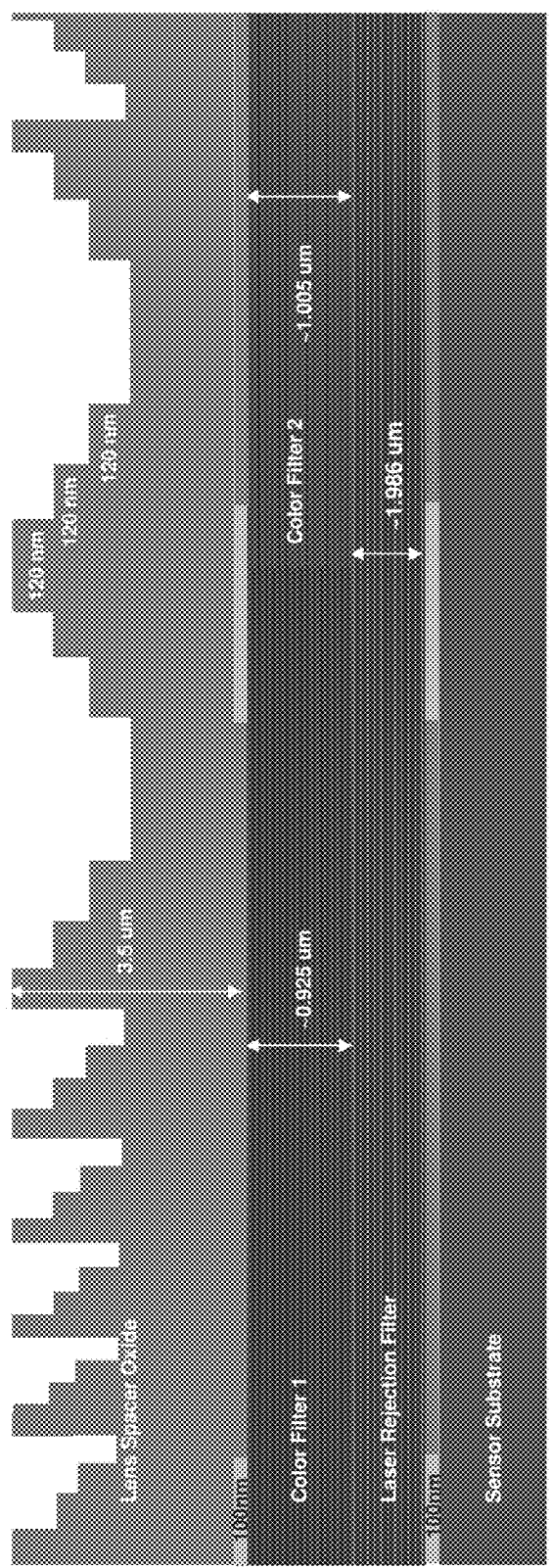
Figure 26L:
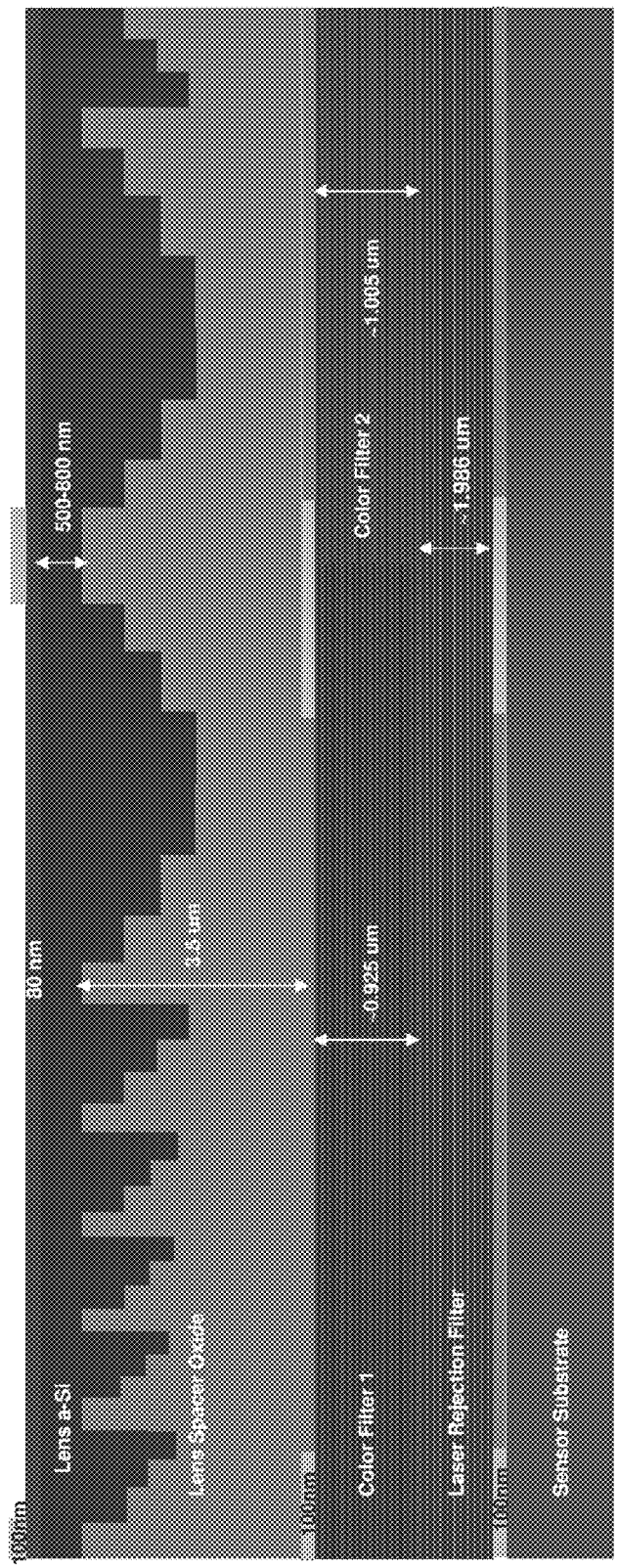
Figure 26N:
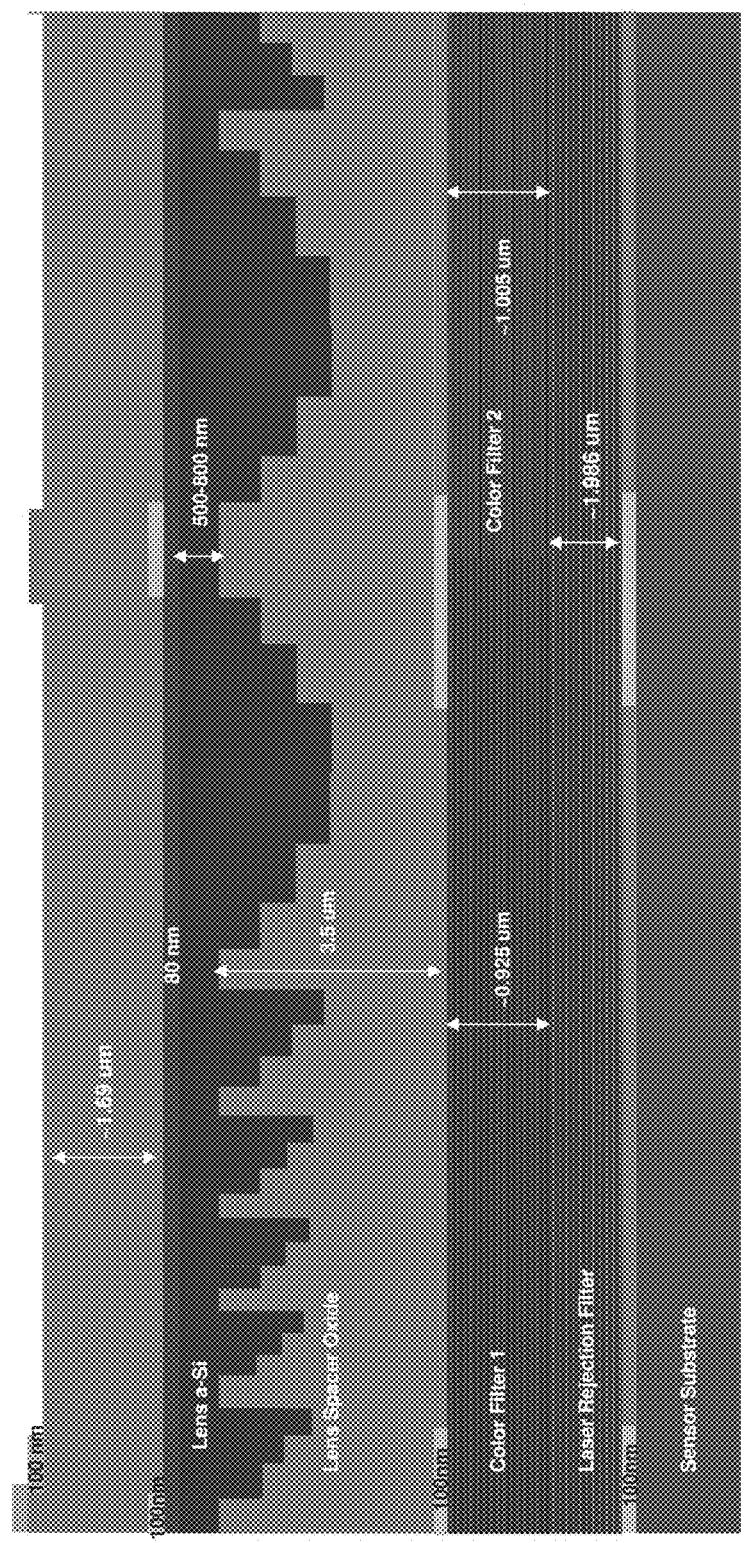
Figure 26P:
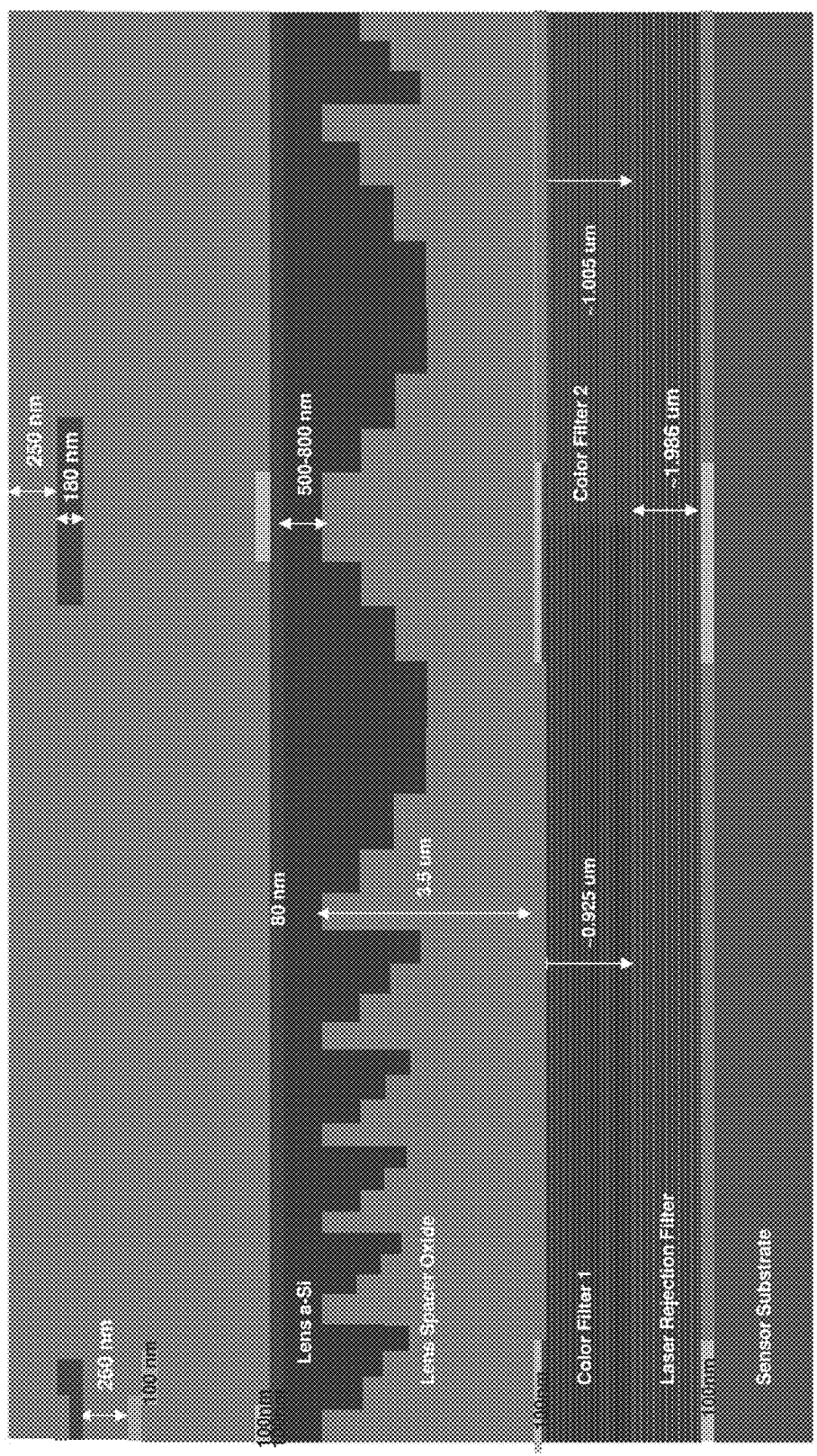
Figure 26R:
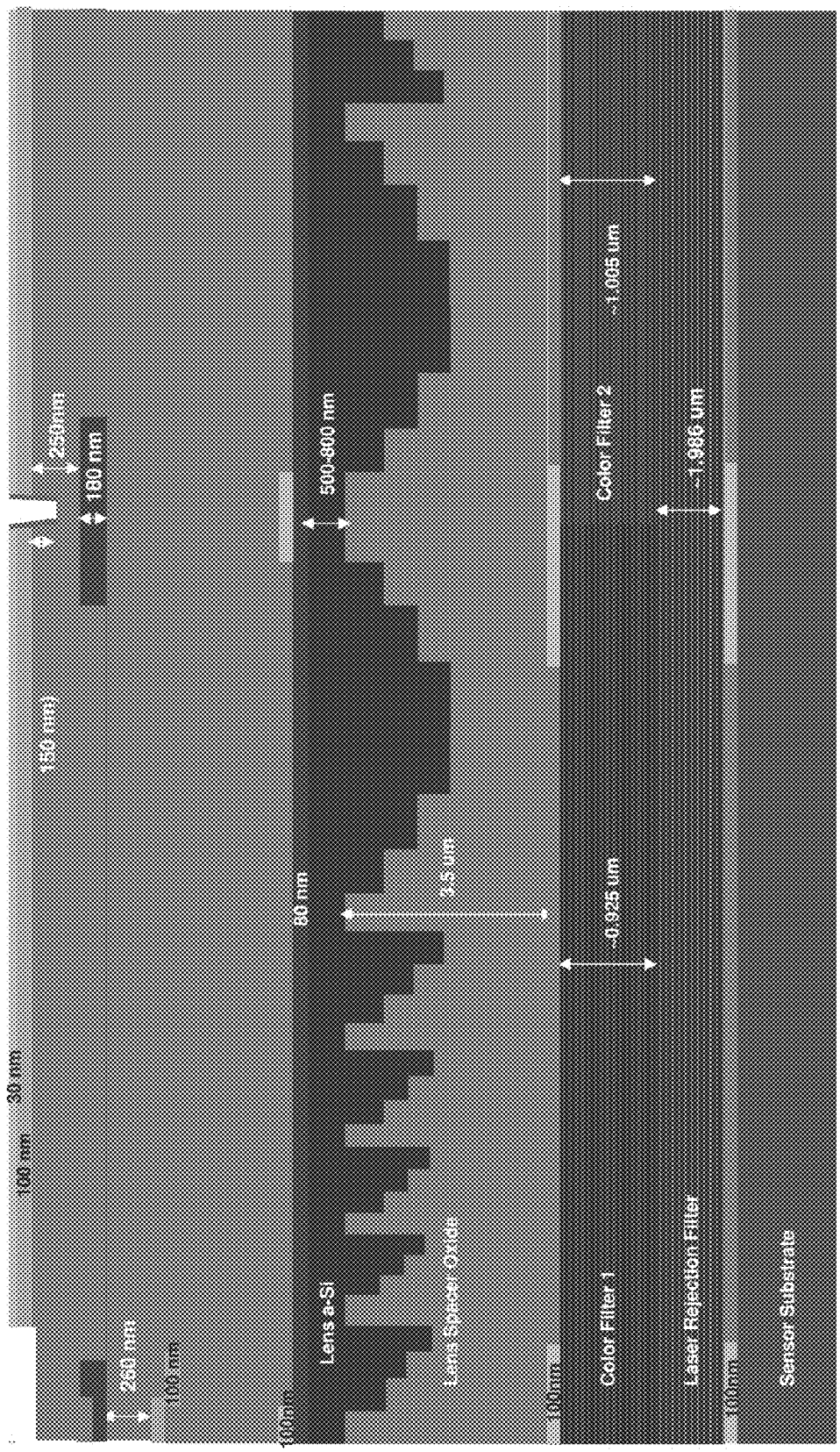

An exemplary semiconductor fabrication process according to one aspect of the instant invention is shown in FIGS. 26A-26R, which illustrate fabrication of an array of integrated analytical devices comprising a diffractive beam shaping element to spatially separate light emitted from a nanoscale emission volume and direct the spatially-separated light through a plurality of color filters to a plurality of sensing regions within a detector layer.

In the exemplary methods, the process begins with a clean semiconductor substrate layer, preferably an integrated CMOS detector layer, although the array could be designed to be attached to a separate detector device. Accordingly, the substrate layer can be of any suitable rigid material with sufficient transparency to light emitted from the reaction well. For examples of appropriate detector layers, see *CMOS Imagers From Phototransduction to Image Processing* (2004) Yadid-Pecht and Etienne-Cummings, eds.; Springer; *CMOS/CCD Sensors and Camera Systems* (2007) Holst and Lomheim; SPIE Press.

The surface of the substrate can be prepared for deposition by, for example, a wet strip process or other suitable cleaning step. Bond pads are opened through passivation of the SiN layer, and the surface is filled with oxide and planarized as shown in steps 1-3 of FIG. 26A.

The sensor substrate layer is next patterned with oxide to generate pattern zero layer alignment marks, as shown in steps 4-6 of FIG. 26A. The patterning aligns to CMOS top metal alignment marks, and zero marks the lowest level alignment layer used for subsequent stack patterning. Aperture 1 is deposited as shown in steps 7-12 of FIG. 26A. As noted in more detail above, this layer is used to screen out low angle signal noise from the diffractive beam shaping element. In addition, the aperture 1 layer can also decorate zero marks to make it more easily visible for subsequent alignments. In this example, the aperture layer is composed of titanium nitride and is approximately 100 nm thick. A graphical representation of the sensor substrate and aperture 1 layer is shown in FIG. 26B.

The laser rejection filter layer is next deposited, as shown in steps 13-15 of FIG. 26C. The filter comprises alternating layers of amorphous silicon and silicon dioxide, deposited as shown. A graphical representation of the sensor substrate, aperture 1 layer, and laser rejection layer is shown in FIG. 26D. Note that step 14 also includes deposition of CF1, the first portion of the color filtration layer. This layer is not shown in FIG. 26D.

The color filtration layer is prepared on top of the laser rejection filter, as shown in steps 16-26 of FIG. 26E. For this example, there are two separate sensing regions on the detector layer for each device of the array, so the color filtration layer in each device comprises two different color filters, CF1 and CF2, as shown graphically in FIG. 26F. The filters themselves comprise alternating layers of amorphous silicon and silicon dioxide, deposited as shown. Color filter CF1 is deposited as part of the laser rejection filter deposition. It is patterned and etched in steps 16-19 of the process. Color filter CF2 is deposited in step 20 of the process, and is patterned and etched in steps 22-25. A graphical representation of the sensor substrate, aperture 1 layer, laser rejection filter layer, and color filtration layer is shown in FIG. 26F. In this example, filters CF1 and CF2 differ only in 2 oxide layers in thickness.

The second aperture layer in this example, aperture 2, is prepared as shown in steps 27-32 of FIG. 26G, and the lens spacer oxide layer is prepared on top of this layer as shown in steps 33-36. A graphical representation of the sensor substrate, aperture 1 layer, laser rejection layer, color filtration layer, aperture 2 layer, and lens spacer oxide layer is shown in FIG. 26H.

The lens element layer, which comprises a diffractive beam shaping element, is prepared by lithographic patterning of the lens space oxide layer, as shown in steps 37-46 of FIG. 26I, and then deposition of a carbon-rich amorphous silicon and polishing, as shown in steps 47-48 of FIG. 26I. A graphical illustration of the intermediate substrate formed after lithographic patterning of the lens spacer oxide layer and before deposition of the carbon-rich amorphous silicon is provided in FIG. 26J.

The patterned, filled, and polished lens layer is next patterned, deposited with titanium nitride, and patterned again to form aperture 3, as illustrated in steps 49-56 of FIG. 26K. The resultant substrate, which includes sensor substrate, aperture 1 layer, laser rejection filter layer, color filtration layer, aperture 2 layer, lens spacer oxide layer, lens layer, and aperture 3 layer is illustrated graphically in FIG. 26L.

Subsequent steps 57-68, as provided in FIG. 26M, represent the deposition of a reflector oxide layer. The result of this deposition is illustrated in FIG. 26N.

An excitation waveguide layer is added to the substrate as shown steps 69-78 of FIG. 26O. In this example, the material comprising the silicon nitride waveguide is deposited in step 69, the waveguide is etched in steps 71 and 74, and the oxide cladding is deposited in steps 76 and 78. The result of these process steps are illustrated graphically in FIG. 26P, which includes sensor substrate, aperture 1 layer, laser rejection filter layer, color filtration layer, aperture 2 layer, lens spacer oxide layer, lens layer, aperture 3 layer, and the waveguide layer.

Fabrication of the zero-mode waveguide (ZMW) layer is shown in steps 79-91 of FIG. 26Q. Specifically, this figure shows the deposition of the aluminum/titanium nitride surface layer in step 79, and the subsequent lithographic opening of the ZMW hole in step 86. The result of the addition of this layer is illustrated graphically in FIG. 26R, which includes all of the above layers and also the ZMW/nanowell layer. It should be noted that the dimensions shown in any of the views of FIGS. 26A-26R are for purposes of illustration only, and should not be taken to be limiting in any way.

After all other process flow steps are complete, the arrays are treated to remove all residues using a cleaning process step. Additional steps can include, for example, deep etching steps to generate contacts to the CMOS bond pads and to couple the arrays to other components of the device.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method for producing an array of integrated analytical devices comprising:
   providing a substrate layer, wherein the substrate layer is a rigid inorganic material;
   depositing a laser rejection filter element layer on the substrate layer;
   depositing a color filtration layer on the laser rejection filter element layer, wherein the color filtration layer comprises 2 to 9 color filtration elements per analytical device, each color filtration element specific for a range of light wavelengths;

depositing a lens element layer on the color filtration layer, wherein the lens element layer comprises a diffractive beam shaping element for each analytical device;

depositing an excitation waveguide layer on the lens element layer;

optionally depositing a first aperture layer on the substrate layer, the color filtration layer, or the lens element layer;

depositing a nanowell layer on the excitation waveguide layer; and patterning and etching the nanowell layer to define a nanowell for each analytical device;

wherein the diffractive beam shaping element is configured to spatially separate light emitted from the nanoscale emission volume into a plurality of beams and to direct the spatially-separated light beams through the color filtration elements.

2. The method of claim 1, wherein there are 2 color filtration elements per integrated analytical device.

3. The method of claim 1, wherein the integrated analytical devices are configured to distinguish four different detectable signal events.

4. The method of claim 1, wherein the diffractive beam shaping element is a hybrid lens.

5. The method of claim 1, wherein the diffractive beam shaping element comprises a Fresnel lens.

6. The method of claim 1, wherein the diffractive beam shaping element comprises amorphous silicon.

7. The method of claim 1, wherein the color filtration elements are dichroic filters.

8. The method of claim 1, wherein the color filtration elements are thin-film interference filters.

9. The method of claim 1, wherein the color filtration elements comprise amorphous silicon and silicon oxide.

10. The method of claim 1, wherein the color filtration elements are absorption filters.

11. The method of claim 1, further comprising:
depositing a second aperture layer on the substrate layer, the color filtration layer, or the lens element layer.

12. The method of claim 11, further comprising:
depositing a third aperture layer on the substrate layer, the color filtration layer, or the lens element layer.

13. The method of claim 1, wherein the first aperture layer comprises titanium nitride.

14. The method of claim 1, wherein the excitation waveguide layer comprises at least one waveguide excitation source, and the nanowell of each analytical device is patterned and etched directly above the waveguide excitation source.

15. The method of claim 1, wherein the substrate layer comprises a plurality of sensing regions per analytical device, the excitation waveguide layer comprises at least one waveguide excitation source, and the sensing regions are collinear with respect to the waveguide excitation source.

16. The method of claim 1, wherein the substrate layer comprises a plurality of sensing regions per analytical device, the excitation waveguide layer comprises at least one waveguide excitation source, and the sensing regions are not collinear with respect to the waveguide excitation source.

17. The method of claim 1, wherein the substrate layer comprises a plurality of sensing regions per analytical device, the excitation waveguide layer comprises at least one waveguide excitation source, and the sensing regions are diagonal with respect to the waveguide excitation source.

18. The method of claim 1, wherein the substrate layer comprises a plurality of sensing regions per analytical device, the excitation waveguide layer comprises at least one waveguide excitation source, and the sensing regions are perpendicular with respect to the waveguide excitation source.

19. The method of claim 1, wherein the excitation waveguide layer comprises a plurality of waveguide excitation sources.

20. The method of claim 19, wherein the waveguide excitation sources are oriented parallel to one another.

21. The method of claim 19, wherein the nanowell of each analytical device is patterned and etched directly above one of the waveguide excitation sources.

22. The method of claim 19, wherein the nanowells in the array of analytical devices are arranged in a regular grid pattern.

23. The method of claim 19, wherein the nanowells in the array of analytical devices are arranged in an offset grid pattern.

24. The method of claim 19, wherein the substrate layer comprises a plurality of sensing regions per analytical device, and the sensing regions are collinear with respect to the waveguide excitation sources.

25. The method of claim 19, wherein the substrate layer comprises a plurality of sensing regions per analytical device, and the sensing regions are not collinear with respect to the waveguide excitation sources.

26. The method of claim 19, wherein the substrate layer comprises a plurality of sensing regions per analytical device, and the sensing regions are diagonal with respect to the waveguide excitation sources.

27. The method of claim 1, wherein the diffractive beam shaping element of each analytical device is configured to collimate light emitted from the nanowell of each analytical device.

28. The method of claim 1, wherein the substrate layer comprises a plurality of rectangular sensing regions per analytical device.

29. The method of claim 1, wherein the substrate layer comprises a plurality of square sensing regions per analytical device.

30. The method of claim 1, wherein the substrate layer comprises a CMOS sensor.

31. The method of claim 1, wherein the method produces an array of at least 1,000, at least 10,000, at least 100,000, at least 1,000,000, or at least 10,000,000 integrated analytical devices.

32. The method of claim 1, wherein the nanowell penetrates into the upper cladding of the excitation waveguide layer.

* * * * *